(12) United States Patent
Echalier et al.

(10) Patent No.: US 10,203,328 B2
(45) Date of Patent: Feb. 12, 2019

(54) CSN5 POLYPEPTIDES AND USES THEREOF FOR SCREENING THERAPEUTIC AGENTS

(71) Applicant: University of Leicester, Leicester (GB)

(72) Inventors: Aude Echalier, Leicester (GB); Christian Dumas, Montpellier (FR); Melissa Birol, Philadelphia, PA (US)

(73) Assignee: University of Leicester, Leicester (GB)

( * ) Notice: Subject to any disclaimer, the term of this patent is extended or adjusted under 35 U.S.C. 154(b) by 0 days.

(21) Appl. No.: 15/443,362

(22) Filed: Feb. 27, 2017

(65) Prior Publication Data
US 2017/0242009 A1 Aug. 24, 2017

Related U.S. Application Data

(63) Continuation of application No. 14/435,375, filed as application No. PCT/EP2013/071408 on Oct. 14, 2013, now abandoned.

(30) Foreign Application Priority Data

Oct. 12, 2012 (EP) .................... 12306251

(51) Int. Cl.
| | |
|---|---|
| *G01N 33/573* | (2006.01) |
| *C12N 9/48* | (2006.01) |
| *G01N 33/68* | (2006.01) |
| *C07K 14/47* | (2006.01) |
| *C12N 9/78* | (2006.01) |

(52) U.S. Cl.
CPC .......... *G01N 33/573* (2013.01); *C07K 14/47* (2013.01); *C12N 9/48* (2013.01); *C12N 9/78* (2013.01); *C12Y 304/00* (2013.01); *G01N 33/6872* (2013.01); *C12Y 305/00* (2013.01); *G01N 2333/948* (2013.01); *G01N 2500/02* (2013.01); *G01N 2500/04* (2013.01); *G01N 2500/20* (2013.01)

(58) Field of Classification Search
CPC ......... C12N 9/48; C12N 9/78; C12Y 304/00; C12Y 305/00; C07K 14/47; G01N 2500/02; G01N 33/573; G01N 33/6872; G01N 2333/948; G01N 2500/04; G01N 2500/20

See application file for complete search history.

(56) References Cited

U.S. PATENT DOCUMENTS

| | | | |
|---|---|---|---|
| 4,861,719 | A | 8/1989 | Miller |
| 5,278,056 | A | 1/1994 | Bank et al. |
| 5,882,877 | A | 3/1999 | Gregory et al. |
| 6,013,516 | A | 1/2000 | Verma et al. |
| 7,279,317 | B2 | 10/2007 | Deshaies et al. |
| 2003/0153097 | A1 | 8/2003 | Deshaies et al. |

FOREIGN PATENT DOCUMENTS

| | | |
|---|---|---|
| WO | 94/19478 A1 | 9/1994 |
| WO | 95/14785 A1 | 6/1995 |
| WO | 96/22378 A1 | 7/1996 |
| WO | 02/055536 A2 | 7/2002 |
| WO | 2009/073069 A2 | 6/2009 |

OTHER PUBLICATIONS

Ambroggio et al, "JAMM: A Metalloprotease-Like Zinc Site in the Proteasome and Signalosome," PLoS Biol. 2(1):E2. (2004).
Cope et al., "Role of Predicted Metalloprotease Motif of Jab1/Csn5 in Cleavage of Nedd8 From Cull," Science 298 (5593):608-611 (2002).
Dumas & van der Lee, "Macromolecular Structure Solution by Charge Flipping," Acta Crystallogr. D. Biol. Crystallogr. D64(Pt 8):864-873 (2008).
Fang et al., "Characterization of the Human COP9 Signalosome Complex Using Affinity Purification and Mass Spectrometry," J. Proteome Res. 7(11):4914-4925 (2008).
Freilich et al., "The COP9 Signalosome is Essential for Development of *Drosophila melanogaster*," Curr. Biol. 9(20):1187-1190 (1999).
Fukumoto et al., "Small Jab1-Containing Subcomplex is Regulated in an Anchorage- and Cell Cycle-Dependent Manner, Which is Abrogated by Ras Transformation," FEBS Lett. 579(5):1047-1054 (2005).
Ho & Agard, "Probing the Flexibility of Large Conformational Changes in Protein Structures Through Local Perturbations," PLoS Comput. Biol. 5 (4):e1000343 (2009).
Holm & Rosenstrom, "Dali Server: Conservation Mapping in 3D," Nucleic Acids Res. 38(Web Server issue):W545-549 (2010).
Kapelari et al., "Electron Microscopy and Subunit-Subunit Interaction Studies Reveal a First Architecture of COP9 Signalosome," J. Mol. Biol. 300(5):1169-1178 (2000).
Kato & Yoneda-Kato, "Mammalian COP9 Signalosome," Genes Cells 14(11):1209-1225 (2009).
Kouvaraki et al. "Potential Role of Jun Activation Domain-Binding Protein 1 as a Negative Regulator of p27kip1 in Pancreatic Adenocarcinoma," Cancer Res. 66(17):8581-8589 (2006).
Krissinel & Henrick, "Inference of Macromolecular Assemblies From Crystalline State," J. Mol. Biol. 372(3):774-797 (2007).
Kwok et al., "*Arabidopsis* Homologs of a c-Jun Coactivator are Present Both in Monomeric Form and in the COP9 Complex, and Their Abundance Is Differentially Affected by the Pleiotropic cop/det/fus Mutations," Plant Cell 10(11):1779-1790 (1998).
Maytal-Kivity et al., "MPN+, a Putative Catalytic Motif Found in a Subset of MPN Domain Proteins From Eukaryotes and Prokaryotes, Is Critical for Rpn11 Function," BMC Biochem. 3:28 (2002).
McCoy et al., "Phaser Crystallographic Software," J. Appl. Crystallogr. 40(Pt 4):658 (2007).
Mundt et al., "Deletion Mutants in COP9/signalosome Subunits in Fission Yeast *Schizosaccharomyces pombe* Display Distinct Phenotypes," Mol. Biol. Cell 13(2):493-502 (2002).
Oron et al., "COP9 Signalosome Subunits 4 and 5 Regulate Multiple Pleiotropic Pathways in *Drosophila melanogaster*," Development 129(19):4399-4409 (2002).

(Continued)

*Primary Examiner* — Gregory S Emch
(74) *Attorney, Agent, or Firm* — LeClairRyan PLLC

(57) ABSTRACT

The present invention relates to mutated CSN5 polypeptides and their use in a method of screening modulators of CSN5 activity that could be used as therapeutic agents.

3 Claims, No Drawings

Specification includes a Sequence Listing.

(56) References Cited

OTHER PUBLICATIONS

Pan et al., "Jab1/CSN5 Negatively Regulates p27 and Plays a Role in the Pathogenesis of Nasopharyngeal Carcinoma," Cancer Res. 72(7):1890-1900 (2012).
Pena et al., "Structure of a Multipartite Protein-Protein Interaction Domain in Splicing Factor prp8 and Its Link to Retinitis Pigmentosa," Mol. Cell 25(4):615-624 (2007).
Pettersen et al., "UCSF Chimera—A Visualization System for Exploratory Research and Analysis," J. Comput. Chem. 25(13)1605-1612 (2004).
Ramage et al., "Synthetic, Structural and Biological Studies of the Ubiquitin System: The Total Chemical Synthesis of Ubiquitin," Biochem. J. 299( Pt 1):151-158 (1994).
Sanches et al., "The Crystal Structure of the Human Mov34 MPN Domain Reveals a Metal-Free Dimer," J. Mol. Biol. 370(5):846-855 (2007).
Sato et al., "Structural Basis for Specific Cleavage of Lys 63-Linked Polyubiquitin Chains," Nature 455(7211):358-362 (2008).
Serino et al.. "*Arabidopsis* cop8 and fus4 Mutations Define the Same Gene That Encodes Subunit 4 of the COP9 Signalosome," Plant Cell 11(10):1967-1980 (1999).
Shackleford & Claret, "JAB1/CSN5 : A New Player in Cell Cycle Control and Cancer," Cell. Div. 5:26 (2010).
Sharon et al., "Symmetrical Modularity of the COP9 Signalosome Complex Suggests its Multifunctionality," Structure 17(1):31-40 (2009).
Tomoda et al., "The Cytoplasmic Shuttling and Subsequent Degradation of p27Kip1 Mediated by Jab1/CSN5 and the COP9 Signalosome Complex," J. Biol. Chem. 277(3):2302-2310 (2002).
Tomoda et al., "Multiple Functions of Jab1 are Required for Early Embryonic Development and Growth Potential in Mice," J. Biol. Chem. 279(41):43013-43018 (2004).
Tran et al., "Structure of the Jab1/MPN Domain and Its Implications for Proteasome Function," Biochemistry 42(39):11460-11465 (2003).
Wei et al., "The COP9 Signalosome: More Than a Protease," Trends Biochem. Sci. 33(12):592-600 (2008).
Whitby et al., "Crystal Structure of the Human Ubiquitin-Like Protein NEDD8 and Interactions With Ubiquitin Pathway Enzymes," J. Biol. Chem. 273(52):34983-34991 (1998).
Zhang et al., "The Crystal Structure of the MPN Domain From the COP9 Signalosome Subunit CSN6," FEBS Letters 586(8):1147-1153 (2012).
Fukumoto et al., "Depletion of Jab1 Inhibits Proliferation of Pancreatic Cancer Cell Lines," FEBS Letters 580(250):5836-5844 (2006).
Mikus et al., "COPing With Hypoxia," Seminars in Cell Developmental Biology 16(4-5):462-473 (2005).
Tanguy et al., "CSN5 Binds to Misfolded CFTR and Promotes Its Degradation," Biochimica et Biophysica Acta. Molecular Cell Research 1783(6):1189-1199 (2008).
International Search Report and Written Opinion for corresponding PCT/EP2013/071408 (dated Feb. 3, 2014).
GenBank Accession No. AK331742 submitted Jun. 25, 2009.
Kawaura et al., "Assessment of Adaptive Evolution Between Wheat and Rice as Deduced from Full-Length Common Wheat cDNA Sequence Data and Expression Patterns," BMC Genomics 10:271 (2009).
Echalier et al., "Insights Into the Regulation of the Human COP9 Signalosome Catalytic Subunit, CSN5/Jab1," PNAS 110(4):1273-1278 (2013).

CSN5 POLYPEPTIDES AND USES THEREOF FOR SCREENING THERAPEUTIC AGENTS

This application is a continuation of U.S. patent application Ser. No. 14/435,375, filed Apr. 13, 2015, is a national stage application under 35 U.S.C. § 371 of PCT Application No. PCT/EP2013/071408, filed Oct. 14, 2013, which claims the benefit of EP 12306251.5, filed Oct. 12, 2012, which are hereby incorporated by reference in their entirety.

FIELD OF THE INVENTION

The present invention relates to CSN5 polypeptides and uses thereof for screening therapeutic agents.

BACKGROUND OF THE INVENTION

Cell-signaling processes mediated by ubiquitinylation, the post-translational covalent conjugation of ubiquitin molecules, are of prime importance for cellular activity and particularly for protein turnover. Ubiquitin-ligase enzymes, E3s, are responsible for the last step of the ubiquitinylation reaction. The E3 cullin-RING ubiquitin ligases (CRLs) represent the main ubiquitin ligase family. Among several factors that regulate CRL activity, cullin neddylation/deneddylation cycles are central (1).

The COP9 signalosome (CSN), a large multiprotein complex that resembles the 19S lid of the 26S proteasome, plays a central role in the regulation of the E3-cullin RING ubiquitin ligases (CRLs). Due to the fact that a large number of proteins are ubiquitinylated by CRLs, the COP9 signalosome (CSN) is implicated in the control of a significant proportion of the proteome, including pro-oncogenes (for example Myc), tumor suppressors (for example p53) and other important cellular protagonists. Different biological and biochemical functions of the CSN complex have been studied over the years, but by far the most studied is its role as a CRL deneddylase. The catalytic activity of the CSN complex, carried by subunit 5 (CSN5/Jab1), resides in the deneddylation of the CRLs, that is the hydrolysis of the cullin-Nedd8 isopeptide bond. Structurally, the CSN is an eight-subunit complex of about 320 kDa (six PCI (proteasome COP9 eIF3)-based subunits and two Mpr1-Pad1-N-terminal [MPN]-containing subunits). Subunit 5 (CSN5), one of the MPN-containing subunits, carries a zinc-dependent isopeptidase catalytic centre that contains a JAMM (Jab1/MPN/Mov34) motif (also known as MPN+ motif; (2)). Recent detailed studies suggested that the organization of the CSN complex resembles that of the 26S proteasome lid (3), with the deubiquitinase enzyme Rpn11 being the equivalent of the deneddylating subunit CSN5 (2, 4).

The CSN, implicated in various cellular functions, ranging from cell cycles, to circadian rhythm, to immunity, is a very well conserved multi-protein complex in eukaryotes, from plants to mammalian cells. Its importance in cellular functions has been highlighted by genetic studies (5). The physiology of the CSN in normal cells has been well researched, and many studies have found a strong link between the CSN and cancers (6). Intriguingly, the CSN cancer implication is attributable to mainly CSN5, which is located on human chromosome 8q—itself often amplified in cancers.

Smaller forms of the holo-CSN complex, with variable compositions, have been found in vivo (7-11). Although important in cell cycle progression, these sub-CSN complexes have not yet been fully functionally characterized (12). It is interesting that, as alluded to for Rpn11 in the context of the proteasome lid (4), CSN5 is found in two forms, a holo-CSN-associated form that is catalytically active and a holo-CSN-independent state void of isopeptidase activity (2, 3). The modularity and topology of the CSN complex have been explored in vitro by non-denaturing mass spectrometry (MS), which revealed that CSN5 is a peripheral subunit that can homo-dimerize outside of the CSN complex and interacts mostly with the other MPN-containing subunit, CSN6, in the context of the CSN complex (3). The potential interactions of CSN5 with other CSN subunits, namely CSN1, CSN2, CSN4 and CSN7, have been highlighted in earlier reports (1, 8, 13, 14).

Whereas CSN-dependent CSN5 displays isopeptidase activity, it is intrinsically inactive in other physiologically relevant forms. To elucidate the molecular regulation of CSN5 activity, the inventors structurally and functionally characterized it in its CSN-independent form by X-ray crystallography, molecular dynamics (MD) simulations, and in vitro studies. Furthermore, the invention provides a preliminary glimpse into the rational screening of small molecules, antibodies, peptides, pseudopeptide, and polypeptides inhibitors of CSN5 isopeptidase activity.

SUMMARY OF THE INVENTION

The present invention relates to mutated CSN5 polypeptides and their use in a method of screening modulators of CSN5 activity that could be used as therapeutic agents.

DETAILED DESCRIPTION OF THE INVENTION

The inventors analyzed the crystal structure of human CSN5 in its catalytically inactive form to illuminate the molecular basis for its activation state. The inventors demonstrate that CSN5 presents a catalytic domain that brings essential elements to understand its activity control. Although the CSN5 active site is catalytically competent and compatible with di-isopeptide binding, the Ins-1 segment obstructs access to its substrate binding-site and structural rearrangements are necessary for the substrate pocket formation. Detailed study of CSN5 by MD unveils signs of flexibility and plasticity of the Ins-1 segment. These analyses led to the identification of a molecular trigger implicated in the active/inactive switch that is sufficient to impose on CSN5 an active isopeptidase state. The inventors demonstrate that a single mutation in the Ins-1 segment restores a deneddylase activity. This invention presents the first detailed insights into CSN5 regulation. These experiments contributed to the design of a constitutively active form of CSN5, shedding lights on its activation control mechanism at a molecular level.

The inventors demonstrated that the substitution of the Arg106 amino acid residue by another amino acid residue excepting proline restores a constitutive isopeptidase activity and the ability for CSN5 to recruit Nedd8.

The inventors also demonstrated that the two subunits of the COP9 signalosome CSN5 and CSN6 associate to form a stable heterodimer. The inventors demonstrated that CSN6 is able to significantly enhance CSN5 isopeptidase and deneddylase activity, this effect is consistently more marked in the context of the activatory mutant form of CSN5, CSN5 R106T than of the WT form.

Definitions

As used herein, the term "CSN5" has its general meaning in the art (1-5) and refers to COP9 signalosome complex subunit 5. The term CSN5 is also known as Jab1. Exemplary amino acid sequences of CSN5 are depicted in table A (SEQ ID NO: 1-16). The term also includes the function conservative variants of SEQ ID NO: 1-16.

TABLE A

CSN5 polypeptides.

| Protein name | Species | GI accession number | Sequence number | Position of the critical amino acid residue | Fragment of interest |
|---|---|---|---|---|---|
| CSN5 | Homo sapiens | 119607334 | SEQ ID NO: 1 | 106 | 53-252 |
| CSN5 | Homo sapiens | 119607336 | SEQ ID NO: 2 | 151 | 98-297 |
| CSN5 | Taeniopygia guttata | 197129932 | SEQ ID NO: 3 | 111 | 58-257 |
| CSN5 | Gallus gallus | 86129524 | SEQ ID NO: 4 | 110 | 57-256 |
| CSN5 | Cricetulus griseus | 354501019 | SEQ ID NO: 5 | 108 | 55-254 |
| CSN5 | Crotalus adamanteus | 387015268 | SEQ ID NO: 6 | 109 | 56-255 |
| CSN5 | Mustela putorius furo | 355680616 | SEQ ID NO: 7 | 114 | 61-260 |
| CSN5 | Xenopus laevis | 148233750 | SEQ ID NO: 8 | 104 | 51-250 |
| CSN5 | Tetraodon nigroviridis | 47213973 | SEQ ID NO: 9 | 105 | 52-251 |
| CSN5 | Amblyomma maculatum | 346471157 | SEQ ID NO: 10 | 103 | 50-249 |
| CSN5 | Crassostrea gigas | 405954518 | SEQ ID NO: 11 | 103 | 50-249 |
| CSN5 | Papilio xuthus | 389609837 | SEQ ID NO: 12 | 110 | 57-256 |
| CSN5 | Bombyx mori | 223890174 | SEQ ID NO: 13 | 110 | 57-256 |
| CSN5 | Anopheles gambiae | 347968735 | SEQ ID NO: 14 | 101 | 48-247 |
| CSN5 | Bombus impatiens | 350403594 | SEQ ID NO: 15 | 109 | 56-255 |
| CSN5 | Schistosoma mansoni | 353231618 | SEQ ID NO: 16 | 127 | 75-273 |

As used herein, the term "Function-conservative variants" denotes polypeptides derived from a polypeptide of the invention in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent of protein or amino acid sequence similarity between any two proteins of similar function may vary and may be, for example, from 70% to 99% as determined according to an alignment method such as by the Cluster Method, wherein similarity is based on the MEGALIGN algorithm. A "function-conservative variant" also includes a polypeptide which has at least 20% amino acid identity as determined by BLAST or FASTA algorithms, preferably 40% more preferably 60%, preferably at least 75%, most preferably at least 85%, and even more preferably at least 90%, and which has the same or substantially similar properties or functions as the native or parent protein to which it is compared, and which has the critical amino acid at a position equivalent to the arginine at position 106 in SEQ ID NO: 1.

The amino acid residue critical for the active/inactive switch of the polypeptide of the invention refers to amino acid residue at position equivalent to the conserved arginine at position 106 in SEQ ID NO: 1 which is important in keeping the polypeptide of the invention in a conformation not competent for Nedd8 binding and which is critical for the active/inactive switch of the polypeptide of the invention to allow an active isopeptidase state.

As used herein, the term "CSN6" has its general meaning in the art (1) and refers to COPS signalosome complex subunit 6. Exemplary amino acid sequences of CSN6 are depicted in table B (SEQ ID NO: 17-25). The term also includes the function conservative variants of SEQ ID NO: 17-25

TABLE B

CSN6 polypeptides.

| Protein name | Species | GI accession number | Sequence number | Fragment of interest |
|---|---|---|---|---|
| CSN6 | Homo sapiens | Q7L5N1 | SEQ ID NO: 17 | 31-193 |
| CSN6 | Bos taurus | A6QQ21 | SEQ ID NO: 18 | 28-190 |
| CSN6 | Cricetulus griseus | G3I5F0 | SEQ ID NO: 19 | 25-187 |
| CSN6 | Salmo salar | B9EPB6 | SEQ ID NO: 20 | 20-182 |
| CSN6 | Xenopus laevis | Q6NUC2 | SEQ ID NO: 21 | 22-184 |
| CSN6 | Tetraodon nigroviridis | H3DE60 | SEQ ID NO: 22 | 20-182 |
| CSN6 | Anoplopoma fimbria | C3KHN7 | SEQ ID NO: 23 | 20-182 |
| CSN6 | Crassostrea gigas | K1QRE1 | SEQ ID NO: 24 | 22-178 |
| CSN6 | Drosophila melanogaster | Q9VCY3 | SEQ ID NO: 25 | 38-200 |

Polypeptides of the Invention

The present invention relates to a fragment of a CSN5 polypeptide wherein the amino acid residue critical for the active/inactive switch of the polypeptide was substituted to allow an active isopeptidase state.

In some embodiments the present invention relates to a polypeptide comprising an amino acid sequence ranging from amino acid at position 53 to amino acid at position 252 in SEQ ID NO: 1 wherein the amino acid at position 106 in SEQ ID NO: 1 is substituted by another amino acid, an amino acid sequence ranging from amino acid at position 98 to amino acid at position 297 in SEQ ID NO: 2 wherein the amino acid at position 151 in SEQ ID NO: 2 is substituted by another amino acid, an amino acid sequence ranging from amino acid at position 58 to amino acid at position 257 in SEQ ID NO: 3 wherein the amino acid at position 111 in SEQ ID NO: 3 is substituted by another amino acid, an amino acid sequence ranging from amino acid at position 57 to amino acid at position 256 in SEQ ID NO: 4 wherein the amino acid at position 110 in SEQ ID NO: 4 is substituted by another amino acid, an amino acid sequence ranging from amino acid at position 55 to amino acid at position 254 in SEQ ID NO: 5 wherein the amino acid at position 108 in SEQ ID NO: 5 is substituted by another amino acid, an amino acid sequence ranging from amino acid at position 56 to amino acid at position 255 in SEQ ID NO: 6 wherein the amino acid at position 109 in SEQ ID NO: 6 is substituted by another amino acid, an amino acid sequence ranging from amino acid at position 61 to amino acid at position 260 in SEQ ID NO: 7 wherein the amino acid at position 114 in SEQ ID NO: 7 is substituted by another amino acid, an amino acid sequence ranging from amino acid at position 51 to amino acid at position 250 in SEQ ID NO: 8 wherein the amino acid at position 104 in SEQ ID NO: 8 is substituted by another amino acid, an amino acid sequence ranging from amino acid at position 52 to amino acid at position 251 in SEQ ID NO: 9 wherein the amino acid at position 105 in SEQ ID NO: 9 is substituted by another amino acid, an amino acid sequence ranging from amino acid at position 50 to amino acid at position 249 in SEQ ID NO: 10 wherein the amino acid at position 103 in SEQ ID NO: 10 is substituted by another amino acid, an amino acid sequence ranging from amino acid at position 50 to amino acid at position 249 in SEQ ID NO: 11 wherein the amino acid at position 103 in SEQ ID NO: 11 is substituted by another amino acid, an amino acid sequence ranging from amino acid at position 57 to amino acid at position 256 in SEQ ID NO: 12 wherein the amino acid at position 110 in SEQ ID NO: 12 is substituted by another amino acid, an amino acid sequence ranging from amino acid at position 57 to amino acid at position 256 in SEQ ID NO: 13 wherein the amino acid at position 110 in SEQ ID NO: 13 is substituted by another amino acid, an amino acid sequence ranging from amino acid at position 48 to amino acid at position 247 in SEQ ID NO: 14 wherein the amino acid at position 101 in SEQ ID NO: 14 is substituted by another amino acid, an amino acid sequence ranging from amino acid at position 56 to amino acid at position 255 in SEQ ID NO: 15 wherein the amino acid at position 109 in SEQ ID NO: 15 is substituted by another amino acid, or an amino acid sequence ranging from amino acid at position 75 to amino acid at position 273 in SEQ ID NO: 16 wherein the amino acid at position 127 in SEQ ID NO: 16 is substituted by another amino acid, and function-conservative variants thereof.

The present invention relates to a CSN5 polypeptide wherein the amino acid residue critical for the active/inactive switch of the polypeptide was substituted to allow an active isopeptidase state.

In some embodiments, the present invention relates to a polypeptide comprising an amino acid sequence SEQ ID NO: 1 wherein the amino acid at position 106 in SEQ ID NO: 1 is substituted by another amino acid, an amino acid sequence SEQ ID NO: 2 wherein the amino acid at position 151 in SEQ ID NO: 2 is substituted by another amino acid, an amino acid sequence SEQ ID NO: 3 wherein the amino acid at position 111 in SEQ ID NO: 3 is substituted by another amino acid, an amino acid sequence SEQ ID NO: 4 wherein the amino acid at position 110 in SEQ ID NO: 4 is substituted by another amino acid, an amino acid sequence SEQ ID NO: 5 wherein the amino acid at position 108 in SEQ ID NO: 5 is substituted by another amino acid, an amino acid sequence SEQ ID NO: 6 wherein the amino acid at position 109 in SEQ ID NO: 6 is substituted by another amino acid, an amino acid sequence SEQ ID NO: 7 wherein the amino acid at position 114 in SEQ ID NO: 7 is substituted by another amino acid, an amino acid sequence SEQ ID NO: 8 wherein the amino acid at position 104 in SEQ ID NO: 8 is substituted by another amino acid, an amino acid sequence SEQ ID NO: 9 wherein the amino acid at position 105 in SEQ ID NO: 9 is substituted by another amino acid, an amino acid sequence SEQ ID NO: 10 wherein the amino acid at position 103 in SEQ ID NO: 10 is substituted by another amino acid, an amino acid sequence SEQ ID NO: 11 wherein the amino acid at position 103 in SEQ ID NO: 11 is substituted by another amino acid, an amino acid sequence SEQ ID NO: 12 wherein the amino acid at position 110 in SEQ ID NO: 12 is substituted by another amino acid, an amino acid sequence SEQ ID NO: 13 wherein the amino acid at position 110 in SEQ ID NO: 13 is substituted by another amino acid, an amino acid sequence SEQ ID NO: 14 wherein the amino acid at position 101 in SEQ ID NO: 14 is substituted by another amino acid, an amino acid sequence SEQ ID NO: 15 wherein the amino acid at position 109 in SEQ ID NO: 15 is substituted by another amino acid, or an amino acid sequence SEQ ID NO: 16 wherein the amino acid at position 127 in SEQ ID NO: 16 is substituted by another amino acid, and function-conservative variants thereof.

Typically, the amino acid residue critical for the active/inactive switch of the CSN5 polypeptide or of the fragment of the CSN5 polypeptide is substituted by any amino acid residue excepting proline to allow an active isopeptidase state.

The present invention also relates a kit of parts comprising at least one CSN5 polypeptide according to the invention or a fragment thereof and at least one CSN6 polypeptide or a fragment thereof.

The polypeptides of the invention may be produced by any technique known per se in the art, such as, without limitation, any chemical, biological, genetic or enzymatic technique, either alone or in combination.

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired polypeptide into expression vectors and introduction of such vectors into suitable eukaryotic or prokaryotic hosts that will express the desired polypeptide, from which they can be later isolated using well-known techniques or corresponding cell-free systems (such as *E coli*, wheat germ systems).

Nucleic Acids, Vectors and Recombinant Host Cells of the Invention

The present invention also relates to a nucleic acid molecule encoding polypeptides according to the invention.

A "coding sequence" or a sequence "encoding" an expression product, such as a RNA, peptide, protein, or enzyme, is a nucleotide sequence that, when expressed, results in the production of that RNA, peptide, protein, or enzyme, i.e., the nucleotide sequence encodes an amino acid sequence for that peptide, protein or enzyme. A coding sequence for a protein may include a start codon (usually ATG) and a stop codon.

These nucleic acid molecules may be obtained by conventional methods well known to those skilled in the art, in particular by site-directed mutagenesis of the gene encoding the native protein. Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule of the invention is associated with suitable elements for controlling transcription (in particular promoter, enhancer and, optionally, terminator) and, optionally translation, and also the recombinant vectors into which a nucleic acid molecule in accordance with the invention is inserted. These recombinant vectors may, for example, be cloning vectors, or expression vectors.

The terms "vector", "cloning vector" and "expression vector" mean the vehicle by which a DNA or RNA sequence (e.g. a foreign gene) may be introduced into a host cell, so as to transform the host and promote expression (e.g. transcription and translation) of the introduced sequence.

Any expression vector for animal cell may be used, as long as a gene encoding a polypeptide or chimeric derivative of the invention can be inserted and expressed. Examples of suitable vectors include pAGE107, pAGE103, pHSG274, pKCR, pSG1 beta d2-4 and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

The invention also includes gene delivery systems comprising a nucleic acid molecule of the invention. This includes for instance viral transfer vectors such as those derived from retrovirus, adenovirus, adeno associated virus, lentivirus, which are conventionally used in gene therapy. This also includes gene delivery systems comprising a nucleic acid molecule of the invention and a non-viral gene delivery vehicle. Examples of non viral gene delivery vehicles include liposomes and polymers such as polyethylenimines, cyclodextrins, histidine/lysine (HK) polymers, etc.

Another object of the invention is also a prokaryotic or eukaryotic host cell genetically transformed with at least one nucleic acid molecule according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

Preferably, for expressing and producing the polypeptides, and in particular the polypeptide according to the invention, eukaryotic cells, in particular mammalian cells, and more particularly human cells, will be chosen.

The construction of expression vectors in accordance with the invention, the transformation of the host cells can be carried out using conventional molecular biology techniques. The polypeptide of the invention, can, for example, be obtained by culturing genetically transformed cells in accordance with the invention and recovering the derivative expressed by said cell, from the culture. They may then, if necessary, be purified by conventional procedures, known in themselves to those skilled in the art, for example by fractionated precipitation, in particular ammonium sulphate precipitation, electrophoresis, gel filtration, affinity chromatography, etc.

In particular, conventional methods for preparing and purifying recombinant proteins may be used for producing the proteins in accordance with the invention.

In some embodiments, the invention relates to a non human transgenic animal transforming with an acid nucleic according to the invention. Typically, said animal is a mouse.

Screening Methods of the Invention

The present invention also relates to polypeptide of the invention for use in a method of screening modulators of CSN5 activity that could be used as therapeutic agents.

The present invention also relates to a method of screening therapeutic agents comprising the steps of:
  i) providing a CSN5 polypeptide according to the invention or a fragment thereof,
  ii) providing at least one CSN5 isopeptidase substrate,
  iii) providing a candidate agent,
  iv) measuring the binding of the substrate using appropriate biophysical techniques and/or measuring the activity of the CSN5 polypeptide,
  v) and positively selecting candidate agents that modulates CSN5 activity.

The inventors demonstrated that CSN6 is able to significantly enhance CSN5 isopeptidase and deneddylase activity.

Accordingly, the present invention also relates to a method of screening therapeutic agents comprising the steps of:
i) providing a CSN5 polypeptide such as a CSN5 polypeptide selected from the group consisting of SEQ ID NO: 1-16, or a CSN5 polypeptide according to the invention or a fragment thereof,
ii) providing a CSN6 polypeptide or a fragment thereof,
iii) providing at least one CSN5 isopeptidase substrate (synthetic or natural),
iv) providing a candidate agent,
v) measuring the binding of the substrate using appropriate biophysical techniques and/or measuring the activity of the CSN5 polypeptide,
vi) and positively selecting candidate agents that modulates CSN5 activity.

Typically, the CSN5 isopeptidase substrates include but are not limited to a C-terminal-Nedd8-peptide (the LRGG tetrapeptide) or Nedd8 peptide linked to a detectable agent i.e. any reporter chemical group such as a fluorescent label (AMC) or a radioactive label (radio-labeled amino acid), or from neddylated proteins such as cullins or cullin fragments.

Typically, the screening method of the invention use standard or high throughput (HTP) assays.

Typically, the candidate agents include but are not limited to small organic molecules, antibodies, peptides or polypeptides.

Methods for measuring the activity of the CSN5 polypeptide are well known in the art. For example, measuring the CSN5 activity involves measuring a constitutive isopeptidase activity, measuring the ability for CSN5 to recruit Nedd8, measuring the CRLs deneddylase activity or determining a Ki on the CSN5 cloned and transfected in a stable manner into a CHO cell line in the presence or absence of the candidate agent. In vitro, ex vivo assays (e.g. cell lysates) and in vivo assays may be used to assess the potency and selectivity of the candidate agents to reduce CSN5 activity. Biophysical techniques such as crystallography may also be used.

Activities of the candidate agents, their ability to bind CSN5 and their ability to inhibit CSN5 activity may be tested using isolated cells, human embryonic kidney cells (HEK), or *Escherichia coli* expressing constitutively active CSN5, CHO cell line cloned and transfected in a stable manner by the constitutively active CSN5.

Cells and *Escherichia coli* expressing wild-type (WT) CSN5 may be used to assess selectivity of the candidate agents.

In one embodiment, the present invention relates to a method of screening therapeutic agents comprising the steps of:
i) providing a CSN5 polypeptide according to the invention or a fragment thereof,
ii) providing a candidate agent,
iii) measuring the binding of the candidate agent to the CSN5 polypeptide using appropriate biophysical techniques,
iv) and positively selecting candidate agents that bind to the CSN5 polypeptide.

In one embodiment, the present invention relates to a method of screening therapeutic agents comprising the steps of:
i) providing a CSN5 polypeptide such as a CSN5 polypeptide selected from the group consisting of SEQ ID NO: 1-16, or a CSN5 polypeptide according to the invention or a fragment thereof,
ii) providing a CSN6 polypeptide or a fragment thereof,
iii) providing a candidate agent,
iv) measuring the binding of the candidate agent to the CSN5 polypeptide using appropriate biophysical techniques,
v) and positively selecting candidate agents that bind to the CSN5 polypeptide.

Methods for measuring the binding of the candidate agent to the CSN5 polypeptide are well known in the art. For example, measuring the binding of the candidate agent to the CSN5 polypeptide may be performed by biophysical techniques such as binding tests (for example and not restricted to: Isothermal calorimetry (ITC), fluorescence anisotropy, Surface Plasmon Resonance (SPR), NMR) and crystallography.

Typically, the candidate agent may be an agent that dissociates the CSN5/CSN6 complex. Measuring CSN5/CSN6 complex dissociation may be performed by biophysical techniques such as Isothermal calorimetry (ITC) and Surface Plasmon Resonance (SPR).

Typically the therapeutic agent screened by the screening method of the invention will be suitable for the treatment of disease or perturbation related to CSN5 inhibition such as cancer.

Kits of the Invention

The invention also relates to a kit for performing the methods as above described, wherein said kit comprises a fragment of a CSN5 polypeptide or a CSN5 polypeptide according to the invention. The kit may also include a fragment of a CSN6 polypeptide or a CSN6 polypeptide. The kit may also include a CSN5 substrate. The kit may also comprise means for measuring the isopeptidase activity level of the CSN5 polypeptide. The kit may also contain other suitably packaged reagents and materials needed for the particular analysis protocol, and standards.

The invention will be further illustrated by the following examples. However, these examples should not be interpreted in any way as limiting the scope of the present invention.

EXAMPLES

Example 1

Material & Methods
Construct Design, Cloning, Expression and Purification.
The human wild-type (WT) and CSN5 mutant proteins were obtained by heterologous expression in *Escherichia coli* (*E. coli*). cDNA coding for full-length (1-334) CSN5 was cloned into the pGEX-6P1 vector (GE Healthcare). Expression trials under standard conditions revealed that the majority of recombinant CSN5 in *Escherichia coli* was expressed in truncated forms ranging from 29 to 31 kDa. The corresponding purified CSN5 fragments were identified using N-terminal sequencing and electrospray-mass spectrometry. The lowest-molecular-weight fragment was assigned the sequence 1-257. Subcloning of the corresponding DNA fragment was performed using the pGEX-6P1 vector. Site directed mutagenesis was performed using the QuikChange Lightning Site-Directed mutagenesis kit (Stratagene) and point mutation oligonucleotides (Eurogentec). All constructs and mutations were checked by DNA sequencing (Beckman Coulter Genomics).

Expression of $CSN5_{1-257}$ wild type (WT) and mutant forms in Rosetta or BL21pLysS *E. coli* cells (Novagen) and purification were performed using standard conditions.

Induced bacterial cells were resuspended in the purification buffer (20 mM Na-2-(N-morpholino)ethanesulfonic acid (Na-MES), pH 6.5, 100 mM NaCl, 0.002% monothioglycerol (MTG)) supplemented with EDTA-free protease inhibitor cocktail (Roche) and were lysed by sonication. Cell lysate was clarified by centrifugation and applied onto a gravity-flow Glutathione Sepharose 4B column (GE Healthcare). Glutathione S-transferase (GST)-tagged $CSN5_{1-257}$ was eluted by 20 mM reduced glutathione in the purification buffer and was cleaved overnight at 4° C. by GST-3C protease. The sample was concentrated and loaded onto a Superdex 75 gel filtration column (GE Healthcare). A final polishing step was used to separate $CSN5_{1-257}$ from contaminating GST. The resulting pure $CSN5_{1-257}$ was concentrated to 10 mg mL-1 and stored at −80° C. until further use. Protein concentrations were measured with a Nanodrop (ThermoScientific) at 280 nm using their theoretical extinction coefficient.

Selenomethionine (SeMet)-labeled $CSN5_{1-257}$ was expressed in methionine-auxotrophic E. coli strain B834 in minimum medium supplemented with SeMet following the manufacturer's instructions (Molecular Dimensions). Although the production yield was smaller, the rest of the 2 purification procedure was unchanged.

Preparation of Rbx1/Nedd8-Cul1-CTP/Cul1-NTD

420 μg of Rbx1/Cul1-CTP/Cul1-NTD were subjected to neddylation using the Enzo Life Sciences neddylation kit. Neddylation reaction mixture was loaded on a Superdex 75 10/300 GL gel filtration column, equilibrated in 20 mM NaMES pH6.5, 200 mM NaCl, 5 mM DTT, to isolate Rbx1/Nedd8-Cul1-CTP/Cul1-NTD. Rbx1/Nedd8-Cul1-CTP/Cul1-NTD containing fractions were pooled and concentrated to 7 mg·mL$^{-1}$ and stored at −80° C. until further use.

Crystallization, Data Collection and Structure Determination

Purified$CSN5_{1-257}$ samples were centrifuged through a 0.2-μm filtration unit and subjected to nanoliter crystallization trials using commercial screening kits. Crystals were grown using the sitting drop vapor diffusion method, mixing equal volumes of the protein and the crystallization well solution (0.1 M Na-HEPES, pH 7.5, 27% PEG3350, 0.7 M KSCN). Diffraction data sets were collected on crystals directly frozen in liquid nitrogen. SeMet-labeled $CSN5_{1-257}$ crystals diffracted to 2.6 Å and belonged to the C-centered monoclinic space group with two molecules in the asymmetric unit. A dataset was collected at 2.6-Å resolution from a SeMet-labeled $CSN5_{1-257}$ crystal at the ID14-EH4 beamline (ESRF, France) and used to solve the structure using the single-wavelength anomalous dispersion (SAD) method. The dataset was reduced and processed (Table 51) using MOSFLM, SCALA and TRUNCATE from the CCP4 software package (12). The completeness in the last resolution shell fell gradually beyond 2.7 Å due to anisotropic diffraction and radiation-induced damage.

The initial substructure determination and phasing at 2.6-Å resolution performed using AutoSol Wizard of the Phenix package (13) were not successful. Twenty-two heavy-atom sites were localized from anomalous differences data using the charge flipping algorithm (14) as implemented in the SUPERFLIP program (15). All selenium sites except two from SeMet alternate conformations and one zinc site were localized using the SUPERFLIP program (root mean square [r.m.s.] deviation of 0.55 Å with the final refined coordinates). This substructure was used for SAD phasing using the PHASER program (16).

Density modification and automatic tracing in the Resolve program of the Phenix package produced a starting model that assigned 67% of total residues and 48% of side chains. There were two molecules per asymmetric unit as related by a local two-fold axis perpendicular to the crystallographic dyad axis. The structure was completed by iterative model building in Coot (17) and refinement in REFMAC (18) using individual restrained thermal factor refinements and weak non-crystallographic symmetry restraints. The final rounds of refinement were performed using Phenix (13) incorporating six Translation/Libration/Screw (TLS) groups per chain, which produced a model with good statistics and geometry (Table 51) as examined with Molprobity (19). The final model consisted of two chains with residues 2-197 and 219-257, two zinc ions, 52 water molecules, and three thiocyanate ions and was refined to an $R_{free}$ value of 27.4% and an R value of 21.6%. All non-Gly residues fell within the allowed regions of the Ramachandran plot.

Molecular Dynamics Simulations

The A chain from the $CSN5_{1-257}$ crystal structure was used as the initial structure for MD simulations on the WT protein and the R106 (T, G and P) variants. The missing loop (residues 198-218) was built using the MODELLER program (20, 21). The models of the variants were prepared by mutating the appropriate R106 residue before the solvation step using the Coot software. The atoms within 10 Å of the mutated residue were minimized. All the water molecules from the initial model were removed except the one bound to the catalytic zinc. Rather than using covalent bonds or harmonic restraints to maintain the zinc environment, the inventors employed the cationic dummy atom approach (21), which imposes orientational constraints for the four zinc ligands (His138, His140, Glu151 and water) in the tetrahedral configuration. The protonation state of the other ionisable side chains was set to their normal values at pH 7. The resulting structure was surrounded by a periodic octahedral box of TIP3P water. This procedure resulted in a total of 4,029 protein atoms, including the zinc ion and the catalytic water molecule, solvated by 17,000-18,500 water molecules. All MD simulations were performed with the AMBER11 program (22) with the ff03 force field parameters (23) and the additional force field for the zinc atom environment (21). Optimization and relaxation of solvent were initially performed by means of energy minimizations and MD simulations while keeping the solute atoms constrained to their initial positions with weak force constants.

After equilibration was established by gradually increasing the temperature from 100 to 300 K for 50 ps, the system was subjected to short (100-ps) MD simulations with decreasing constraints at a constant temperature of 300 K and a constant pressure of 1 bar. The 40-ns production run was conducted with constrained bond lengths involving hydrogen atoms and using the Shake algorithm (24), the Verlet integrator with a 2-fs time step for seven the calculation of forces and Langevin dynamics for temperature control. A cut-off radius of 9 Å was used to compute the non-bonded steric interactions. The electrostatic interactions were calculated with the particle-mesh Ewald method (25). The missing counterions were substituted with a net-neutralizing plasma over the periodic box. The ptraj module in the AmberTools package (26) was used to extract data from trajectories and to analyze structural and dynamic properties. All computations including the minimizations and the MD simulations were performed on a HP Z800 workstation equipped with two GPU Tesla C1060 and quad-core Xeon 2.4 GHz processors.

Rotamerically Induced Perturbations.

Large conformational changes, as those frequently coupled to catalytic function, are occurring in the order of $10^{th}$ of picoseconds to millisecond timescale. Such long computationally demanding MD calculations are thus difficult to simulate. The Rotamerically Induced Perturbation (RIP) method was designed by Ho and Agard (27) to induce large conformational rearrangements of structural segments at the surface of a protein in short simulation times. This new MD approach is particularly useful to identify potentially mobile structural elements or loops. The RIP local thermal excitation of rotameric rotations was applied on each isolated residue in $CSN5_{1-257}$. The kinetic energy transfer to residues in spatial proximity was analyzed to explore the strength of contacts anchoring local segments and reveal their conformational flexibility (28). For each perturbed residue, a 10 ps simulation is produced using the same starting CSN5 monomeric model, equilibrated at 300 K. A RIP perturbation pulse is applied every 100 fs. The MD simulations were performed using the Amber11 package (26) with an GB/SA implicit solvent model and Python scripts implementing the RIP protocol (http://boscoh.com/rip/). The deformability map (average Cα r.m.s. deviation values) generated from the analysis of the various trajectories provides an excellent indicator of conformational flexibility and reveals buried tertiary couplings.

Isopeptidase Assays Using AMC Derived Substrates.

For the isopeptidase assay using LRGG-AMC substrate, GST-tagged $CSN5_{1-257}$ protein and different mutants were diluted to 0.2 μg μL$^{-1}$ in reaction buffer (40 mM Tris-HCl pH8.5, 5% glycerol, 1 mM DTT), in the presence of 250 μM LRGG-AMC. The isopeptidase activity of the ubiquitin specific protease 2 catalytic domain (USP2CD; purchased from Boston Biochem.) was used as a control in the same conditions but at a concentration of 0.02 μg μL$^{-1}$. The effect of zinc chelation was carried out by pre-incubation of CSN5 in the presence of 10 mM ethylene diamine tetraacetic acid (EDTA). The effect of temperature on the isopeptidase activity was evaluated by pre-incubation of the enzymes at 60° C. water bath for 20 min. For the isopeptidase assay using Nedd8-AMC substrate, $CSN5_{1-257}$ protein and different mutants (R106T, R106A, R106G, R106P, E76A, E76A/R106T) prepared in the same conditions were diluted to 0.2 μg μL$^{-1}$ immediately before in the reaction buffer (40 mM Tris-HCl pH8.5, 1 mM DTT). The CSN complex purified from erythrocytes and purchased from Enzo Life Sciences was used at 0.01 μg μL$^{-1}$. The reactions setup on ice were started by the addition of the substrate (2 μM Nedd8-AMC) to the reaction mixture and followed at 28° C. Isopeptidase assays were monitored in duplicate in a 96-well fluorescence plate on a Tecan Saphire, by following the increase of fluorescence intensity ($\lambda_{excitation}$=380 nm; $\lambda_{emission}$=460 nm), i.e. the hydrolysis of the isopeptide bond between LRGG/Nedd8 and AMC.

Deneddylation of Rbx1/Nedd8-Cul1-CTP/Cul1-NTD.

The CSN complex at 4.8 ng μL$^{-1}$, $CSN5_{1-257}$ protein and R106T variant diluted to 0.33 μg μL$^{-1}$ in 20 mM Tris-HCl pH7.5, 50 mM NaCl were incubated in the presence of 38 μM Rbx1/Nedd8-Cul1-CTP/Cul1-NTD 3 hours at 32° C. Proteins separated on a 10% Tris-tricine gel were transferred on a PVDF membrane and a standard Western blotting protocol was carried out using antibodies specific of Nedd8 (Epitomics) at a dilution of 1:500. Both neddylated cullin 1 and Nedd8 released from the hydrolysis of Nedd8-cullin 1 isopeptide bond were visualized upon chemiluminescence revelation by the SuperSignal West Pico Chemiluminescent Substrate kit (Pierce).

Accession Code:

Coordinates and structure factor amplitudes have been deposited in the Protein Data Bank with the accession code 4F70.

Results

Overall Structure and Oligomeric Arrangement

A stable form of CSN5 comprising residues 1-257 ($CSN5_{1-257}$), identified by MS and N-terminal sequencing, was isolated and crystallized. The crystals belong to the monoclinic C-centered space group and diffracted up to 2.6-Å resolution. The crystal structure was therefore solved by selenium-SAD using diffraction data to 2.6 Å. CSN5, which is the fifth CSN subunit and consists of 334 residues, is a c-Jun-activation domain-binding protein 1 (Jab1)/MPN superfamily member with a conserved core MPN domain (51-230) and a JAMM motif (Glu76, His138, His140, Asp151). In addition to the MPN catalytic domain, CSN5 possesses N- and C-terminal regions that tightly pack against the MPN fold and form an extended catalytic domain. The asymmetric unit of $CSN5_{1-257}$ crystal contains a dimer, related by a local two-fold axis perpendicular to the crystallographic two-fold axis, generating also a second dimeric arrangement. The characteristics of each plausible oligomeric arrangement were evaluated by PISA (20), which highlights two types of dimers (A-B and A-A') and a D2 tetramer that bury a total surface area of 2,112, 1,950 and 8,970 Å2, respectively.

CSN5 can Form Homo-Dimers In Vitro

Several lines of evidences in the literature suggest the propensity of CSN5 to form oligomers. Indeed, non-denaturing MS and proteomic evaluations revealed the presence of oligomers in vitro (3, 21). In eukaryotic cells, CSN5 is present in not only the CSN complex, but also in smaller complexes (between 70 and 150 kDa, while the monomer is 29 kDa) that might correspond to CSN5 oligomeric forms (10-12, 22). Together with these evidences described in the literature but not further experimentally probed, the crystal dimer properties led inventors to explore the functional relevance of CSN5 oligomerisation in vitro. To investigate the presence of the oligomeric species, inventor's experimental approach was based on chemical cross-linking, on dynamic light scattering (DLS) and on analytical ultracentrifugation (AUC). The results showed that monomers and dimers were the major species of CSN5 detected in solution. Supported by both in vitro data, these observations suggest that a dimeric CSN5 assembly could be present in solution, in equilibrium with monomeric species. It is noteworthy that other MPN-containing proteins were found to assemble in dimers in the crystals and that each of the described dimers, for which the question of the physiological relevance has not yet been addressed in vivo, proceeds via totally different interfaces (23, 24). As the biological relevance of these assemblies has not been shown, it therefore prevents further comparison in the context of the present findings. Further to these experiments and on the basis of the A-B and A-A' dimer interface analysis, mutations or deletions were designed to selectively weaken these two inter-subunit interactions. Evaluation of the dimer disruption extent was carried out in vitro by DLS. Two leucine residues (Leu237 and Leu240) placed on one side of the helix α4, facing α6, as well as the Arg129 residue were consequently selected. DLS measurements on these interfacial mutants clearly showed a drop in particle diameter as compared to those on the WT protein. This drop, particularly marked between WT and the double mutant L237Q/L240K, is compatible with the transition from A-B dimer to mostly monomeric species. In contrast, the deletion of the C-terminal tail that mediates the A-A' dimer does not affect as much the assembly, further supporting the idea that the A-B dimer is the preponderant assembly in solution. Taken together, these results demonstrate that CSN5 mainly forms biologically relevant dimers of the A-B type, unveiling a new level of regulation in the biology of CSN5. More that 70% of the CSN5 residues involved in this protein-protein interface are highly conserved among the 170 available sequences, further demonstrating that this assembly may be physiologically relevant.

Conserved Rigid MPN Domain is Decorated by CSN5-Specific N- and C-Terminal Extensions The $CSN5_{1-257}$ structure reveals a fold typical to the Jab1/MPN superfamily (23-28). The core of the MPN fold that consists of the central β-sheet and three α-helices (residues 51-224) is largely conserved in the MPN domain-containing structures solved to date, with a mean r.m.s. deviation of 3.2 Å over an average of 124 residues (as calculated by the DALI server (29)) and a mean r.m.s. deviation of 1 Å for the 54 most central residues (as calculated by Chimera (30)), including the recently reported CSN6 structure from *Drosophila* (24). Structural comparison between MPN members revealed that the region spanning from residues 97 to 129 (referred to as Ins-1) displays different conformations in the various MPN members and is sometimes partially unstructured or disordered. It is noteworthy that the lack of electron density for the CSN5 portion consisting of residues 197-219 (corresponding to Ins-2 in the structure of AMSH-LP (27)) prevented accurate modeling and analysis of this segment.

The ensemble of the CSN5-specific N- and C-terminal segments wrap around and make extensive contacts with the conserved MPN domain core. Most MPN proteins structure solved to date display reduced or no N- and C-terminal additions; with the exception of Prp8p structure that has N- and C-terminal extensions of similar size to that of CSN5 (26). However these regions adopt in CSN5, an MPN+/JAMM enzyme and in Prp8p, a scaffolding protein, very different positions and conformations with respect to the core MPN domain.

To complement and extend the structural insights obtained from crystallography, the inventors carried out a series of MD simulations. The CSN5 crystal structure suggests that the central core domain is stable and that some flanking α-helices and loops displaying higher B-factors could be locked into the structure due to the crystal packing. MD simulations of the solvated CSN5 monomer at 300 K for 40 ns confirmed that the core domain is stable and that the residues forming the Ins-2 segment, the loops and the N- and C-terminal ends display the maximum fluctuation compared with the central core domain.

CSN5 Zinc-Binding Site is Catalytically Competent, Similar to Other JAMM-Containing Motifs As the inventors anticipated from other MPN+/JAMM proteases, the CSN5 structure contains one zinc atom. The strictly conserved zinc coordination site is composed of residues from helix α5 and a subset of the central β-sheet (β5, β5-α5, β6 and β7). The zinc is tetrahedrally coordinated to two histidine residues (His138 and His140), one Asp residue (Asp151), and a catalytic water molecule hydrogen bonded to Glu76 and Ser148. The importance of the active site zinc coordinating residues in catalysis had previously been tested by mutagenesis (2). AMSH-LP is the only structural example of an active MPN+/JAMM isopeptidase enzyme that can exist in its unbound form or in complex with its K63-Ub2 substrate (27). Therefore it provides for this enzyme family a model for a catalytically competent active site and for substrate interactions. Comparison of the zinc-binding sites of CSN5 and AMSH-LP revealed that the overall topology of their active sites is conserved. In addition, the position and environment of the Gly76-Lys63 isopeptide, straightforwardly placed in the CSN5 active site, inferred from the AMSH-LP/K63-Ub2 complex, confirmed that CSN5 adopts a catalytically competent geometry. As described similarly for the AMSH-LP/K63-Ub2 structure, the Gly76-Lys63 isopeptide bond, placed in the CSN5 zinc-binding site, is maintained via a hydrogen bond between the Gly76 carbonyl group and the Ser148 side chain hydroxyl group and between the Lys side chain amine and the Glu76 carboxylate. The inventors also investigated the role played by the catalytic zinc ion on the structure and stability of the active site. The side-chain motions of amino acids in the zinc catalytic site were analyzed. Their positions were stable over the course of the MD simulations, and their averaged inter-atomic distances from Zn2+ were in good agreement with those measured from the $CSN5_{1-257}$ and AMSH-LP crystal structures. Taken together, these observations demonstrate that, as in AMSH-LP, the zinc-binding site catalytic residues of CSN5 are in a position and geometry compatible with isopeptidase activity and therefore that the zinc active site conformation of this enzyme in its isolated form is catalytically competent.

Although the CSN5 zinc-binding site and its catalytic residues are very similar to those of AMSH-LP, their active site properties and spatial accessibility have several differentiating features. In particular, the CSN5 Ins-1 region (loop β4-α4 and α4 helix) adopts a radically different topology in CSN5 and in AMSH-LP i.e. two anti-parallel β-strands and a short α-helix (residues 314-339). An additional distinguishing feature of the CSN5 zinc-binding site is the presence in its surroundings of one arginine residue, Arg106, which forms a salt bridge with Asp151. The substitution of Gln352 and Phe355 residues in AMSH-LP with a tyrosine (Tyr143) and a tryptophan (Trp146) residues in CSN5, respectively, reinforces the hydrophobic character of the CSN5 pocket). Tyr143 in CSN5 hydrogen bonds with Glu76, whereas Gln352 in AMSH-LP is orientated towards the solvent. The importance of the interaction between Glu76 and Tyr143 should be further explored because of the role played in substrate positioning by the equivalent of Glu76 in AMSH-LP, Glu292, and the fact that in MD simulations, this hydrogen bond is not maintained during the simulations.

Surroundings of the CSN5 Zinc Catalytic Site is not Competent for Nedd8 Recruitment, without Conformational Rearrangements Two different activation states of CSN5 are described in the literature (2, 3): an active deneddylase in the context of the holo-CSN complex and an inactive form in the isolated subunit. As suggested by the inventor's data the CSN5 active site is poised for catalysis, it thus seemed logical to explore substrate binding and recruitment by this enzyme.

In the crystal structure of the AMSH-LP/K63-Ub2 complex, the two ubiquitin molecules, referred to as proximal and distal, interact with AMSH-LP via numerous electrostatic and hydrophobic interactions (27). The directionality of the isopeptide bond implies that Nedd8 would occupy the site corresponding to the distal ubiquitin in the AMSH-LP/K63-Ub2 structure. The distal ubiquitin molecule mediates the largest interaction surface area and contributes the most to the binding affinity of K63-Ub2 for AMSH-LP. Correct positioning of the K63-Ub2 isopeptide bond in the long recognition groove of AMSH-LP is ensured by interactions between AMSH-LP (in particular, the Ins-1 region, the Ins-2 loop [disordered in CSN5], and the segment between these two insertions) and the proximal and distal ubiquitins. The C-terminal portion of the distal ubiquitin adopts an extended conformation that fits in the substrate binding groove delimitated by two α-helices and a β-hairpin. Ubiquitin and Nedd8 molecules are 58% identical over 76 residues and adopt the same fold (31, 32). The interactions with the last four residues of ubiquitin/Nedd8, preceding the isopeptide bond are likely to be preserved in CSN5. Only one residue, position 72 (arginine and alanine, respectively in ubiquitin and Nedd8) differentiates ubiquitin from Nedd8 in the last 10 residues. Analysis of the AMSH-LP residues implicated in the distal ubiquitin recognition site revealed that more than 50% are conserved or semi-conserved in CSN5. However, most of the residues for which no equivalent could be found in CSN5 belong to the Ins-1 region, which has a very different conformation in the CSN5 and AMSH-LP structures. Consequently, without the structure of CSN5 in its active state, detailed analysis of the substrate binding site in CSN5 is prevented.

Despite the high conservation of the interaction site in CSN5, the conformation of the Ins-1 observed here sterically precludes Nedd8 binding. Extensive structural changes of this segment, which probably confers some of the specificity for Nedd8 ligand would be required to create a fully competent binding site.

An Arginine Residue Contributes to the Control of CSN5 Isopeptidase Activation State The major difference at the active site level between CSN5 and AMSH-LP corresponds to the conformation of the Ins-1 insertion. It is therefore most interesting to note that the Ins-1 segment of CSN5 shows signs of flexibility, as indicated by high B-factor values and the fact that it exhibits significant conformational variability within representatives of the MPN family. Moreover, MD simulations flagged two portions of the Ins-1 region as highly flexible (residues 98-108 and 122-129). The CSN5 segments 100-105 and 108-112, bracketing the residue Arg106, display ample movements opening onto the solvent in MD simulations, whereas Arg106 contributes significantly to the anchoring of the Ins-1 segment to the zinc-binding site via its salt bridge with Asp151. MD studies confirmed the potential importance of Arg106 with this salt bridge being maintained in the 40-ns trajectories. The observations that Arg106 plays a role in CSN5 plasticity were further probed and confirmed by rotamerically induced perturbation (RIP) simulations (33). These data demonstrate that the intrinsic flexibility and plasticity of the Ins-1 region allow major conformational rearrangements to accommodate Nedd8 binding and that Arg106 have here a triggering function for structural rearrangement of the Ins-1 segment.

To evaluate the role of Arg106 as a potentially important protagonist in CSN5 activation switch, the inventors have tested the effect of Arg106 substitution by a threonine (R106T) on CSN5 isopeptidase activity and Nedd8 binding. In agreement with published data in the literature (2, 3), the inventors confirmed that the $CSN5_{1-257}$ WT form is void of isopeptidase activity and showed that the R106T substitution is sufficient to restore constitutive isopeptidase activity against two isopeptidase substrates, LRGG-AMC and Nedd8-AMC. These results demonstrate that the conformational relaxation of the Ins-1 region allows substrate binding and additionally corroborates inventor's analysis on the intrinsic topological competence of the zinc binding site for catalysis.

To complement these activity data, pull-down experiments, using $GST-CSN5_{1-257}$ as the bait and Nedd8 as the target, showed that the WT form was unable to bind Nedd8, whereas the R106T form was. This confirms that releasing the Ins-1 segment from its anchoring point is sufficient to expose a functional binding site for Nedd8. Taken together, these data strongly demonstrate the implication of Arg106 in the active/inactive switch of CSN5.

Discussion

The roles of the CSN complex span from cell cycle control to immunity. Mediated probably through its denedylase activity, the function of the CSN complex is important for cellular homeostasis, as highlighted by its implication in proliferative diseases (reviewed in (5)). The sequence alignment of the CSN catalytic subunit, CSN5, from different organisms reveals highly conserved features throughout the sequence and the evolutionary tree, in agreement with the essentiality of the csn5 gene previously highlighted for several species (*Dictostelium discoideum, Drosophila melanogaster* and *Mus musculus* (1)) and with its catalytic function within the CSN complex. One major means of controlling CSN function is the traffic of the catalytic subunit CSN5, which shuttles between the holo-CSN, sub-CSN complexes, and CSN-independent forms, but displays isopeptidase activity only in the context of the holo-CSN complex (3).

Despite the importance of CSN regulatory mechanisms, they remain largely unknown and poorly understood. The present invention reveals that CSN5 can be found in different oligomeric states in vitro and may predominantly follow a monomer-dimer equilibrium. The interaction between CSN5 and various partners has been investigated in previous studies, but only in its monomeric form (reviewed in (6)). Its assembly in dimers reveals a largely unexplored aspect of the protein regulation and may be relevant in mediating protein-protein interactions and subcellular localization of CSN5.

A second important aspect in CSN5 biology that is addressed in this work is its activation state in the CSN-independent context. To glean insights into CSN5 isopeptidase activity regulation, the inventors used structural biology and in silico MD simulations, which together created a first detailed picture of CSN5 activity control. The crystal structure of CSN5 in a CSN-independent form displays an extended catalytic domain that revealed a number of features, contributing to our understanding of the enzyme's activation and substrate recruitment. In analogy to the structure of AMSH-LP (27), the apo form of CSN5 adopts a zinc-binding site geometry that appears compatible with isopeptidase activity and potentially with binding of the Gly76-Lys63 isopeptide, as extrapolated from the co-crystal structure of AMSH-LP/K63-Ub2 to the CSN5 zinc-binding site. Unlike AMSH-LP/K63-Ub2, however, investigation of the recruitment of Nedd8 by CSN5 revealed that the exosite is not formed in CSN5 and that the Ins-1 segment would require substantial structural rearrangement for Nedd8 to bind. These observations were confirmed by analysis of Ins-1 flexibility and plasticity by in silico simulations. The present invention also helped understanding the molecular events that trigger these conformational changes in CSN5. MD and RIP calculations pointed to a role for the conserved Arg106 in keeping this segment in a conformation not competent for Nedd8 binding. This implication of this residue, validated by in vitro experiments, led to the confirmation that Arg106 is an important protagonist in CSN5 activation switch. Indeed, substitution of this residue by a threonine restores a constitutive isopeptidase activity and the ability for CSN5 to recruit Nedd8.

Integration of CSN5 into the CSN complex and the consequent protein—protein interactions with CSN subunits such as CSN6, as highlighted by non-denaturing MS experiments (3), are likely to play a part in both CSN5 activation and substrate recruitment. Whereas CSN5 is probably the subunit most responsible for Nedd8 association, other CSN components, such as CSN2, have been shown to bind cullins (1). CSN5 incorporation into the CSN complex probably does not lead to global structural reshaping of the enzyme. Instead, the structural changes are likely to be limited to the Ins-1 segment (identified as malleable in our MD calculations), the Ins-2 region (disordered in the crystal), and possibly the C-terminal domain (residues 258-334) to prime the deneddylating molecule for catalysis. Integration of CSN5 in the CSN complex is probably providing the conformational energy necessary for the activation switch.

Taken together, our study results suggest that CSN5 in its CSN-independent form is deficient in substrate recruitment and that a single residue contributes significantly to the activation switch and that its biology might be further complicated by the presence of oligomeric forms. This discovery provides the framework for further biochemical and functional investigations to elaborate on the regulatory pathways in which CSN5 intervenes.

Example 2: Activation of CSN5 Isopeptidase Activity by CSN6

Material & Methods

Expression and purification. For the CSN5 protein (WT and variant forms), the expressions and purifications were carried out using protocols described previously. Solubly expressing CSN6 constructs were designed and CSN6 was expressed as a fusion protein with GST. The purification protocol follows that of CSN5's with a change of the buffer composition (20 mM Tris-HCl pH7.5, 150 mM NaCl).

Activity measurements. The substrates were used at different concentrations (0 to 400 µM for LRGG-AMC; 0 to 20 µM for Nedd8-AMC; 0 to 2 µM for Nedd8-cullin 1; 0 to 100 µM for pro-Nedd8). The buffer used in the activity measurements is composed of 50 mM Tris-HCl pH 7.5, 50 mM NaCl. All the measurements were done at 37° C. on a Tecan Sapphire fluorimeter (except for Nedd8-cullin 1). For the activity measurements corresponding to Nedd8-cullin 1, cullin 1 deneddylation was followed by gel shift assay and the bands were quantified after an anti-Nedd8 Western blot.

Results

Soluble constructs of CSN5 and CSN6 MPN domains were designed and the corresponding protein fragments were successfully expressed in bacteria.

Their spatial proximity in the Cop9 signalosome complex brought us to investigate a possible direct association between these two MPN domain-containing subunits. Indeed the two subunits of the Cop9 signalosome associate to form a gel filtration stable hetero-dimer. Further characterised in terms of affinity and topology, the dissociation constant of the dimer is around 1-5 µM (ITC) and that its organisation could be consistent with that of CSN5 or Mov34 homo-dimer as probed by a mutagenesis analysis.

These results subsequently brought us to evaluate the effect of CSN6 on CSN5 isopeptidase activity. To do so the inventors use three different substrates (two synthetic (LRGG-AMC; Nedd8-AMC) and one natural (Nedd8-cullin 1)) to show that CSN6 is able to significantly enhance CSN5 isopeptidase activity. Interestingly this effect is consistently more marked in the context of the activatory mutant form of CSN5, CSN5 R106T than the WT form.

REFERENCES

1. Wei N, Serino G, & Deng X W (2008) The COP9 signalosome: more than a protease. *Trends Biochem Sci* 33(12):592-600.
2. Cope G A, et al. (2002) Role of predicted metalloprotease motif of Jab1/Csn5 in cleavage of Nedd8 from Cul1. *Science* 298(5593):608-611.
3. Sharon M, et al. (2009) Symmetrical modularity of the COP9 signalosome complex suggests its multifunctionality. *Structure* 17(1):31-40.
4. Maytal-Kivity V, Reis N, Hofmann K, & Glickman M H (2002) MPN+, a putative catalytic motif found in a subset of MPN domain proteins from eukaryotes and prokaryotes, is critical for Rpn11 function. *BMC Biochem* 3:28.
5. Kato J Y & Yoneda-Kato N (2009) Mammalian COP9 signalosome. *Genes Cells* 14(11):1209-1225.
6. Shackleford T J & Claret F X (2010) JAB1/CSN5: a new player in cell cycle control and cancer. *Cell Div* 5:26.
7. Freilich S, et al. (1999) The COP9 signalosome is essential for development of *Drosophila melanogaster*. *Curr Biol* 9(20): 1187-1190.
8. Kwok S F, et al. (1998) *Arabidopsis* homologs of a c-Jun coactivator are present both in monomeric form and in the COP9 complex, and their abundance is differentially affected by the pleiotropic cop/det/fus mutations. *Plant Cell* 10(11):1779-1790.
9. Mundt K E, Liu C, & Carr A M (2002) Deletion mutants in COP9/signalosome subunits in fission yeast *Schizosaccharomyces pombe* display distinct phenotypes. *Mol Biol Cell* 13(2):493-502.
10. Oron E, et al. (2002) COP9 signalosome subunits 4 and 5 regulate multiple pleiotropic pathways in *Drosophila melanogaster*. *Development* 129(19):4399-4409.
11. Tomoda K, et al. (2002) The cytoplasmic shuttling and subsequent degradation of p27Kip1 mediated by Jab1/CSN5 and the COP9 signalosome complex. *J Biol Chem* 277(3):2302-2310. 12. Fukumoto A, Tomoda K, Kubota M, Kato J Y, & Yoneda-Kato N (2005) Small Jab1-containing subcomplex is regulated in an anchorage- and cell cycle-dependent manner, which is abrogated by ras transformation. *FEBS Lett* 579(5):1047-1054.
13. Kapelari B, et al. (2000) Electron microscopy and subunit-subunit interaction studies reveal a first architecture of COP9 signalosome. *J Mol Biol* 300(5):1169-1178.
14. Serino G, et al. (1999) *Arabidopsis* cop8 and fus4 mutations define the same gene that encodes subunit 4 of the COP9 signalosome. *Plant Cell* 11(10):1967-1980.
15. Dumas C & van der Lee A (2008) Macromolecular structure solution by charge flipping. *Acta Crystallogr D Biol Crystallogr* D64(Pt 8):864-873.
16. McCoy A J, et al. (2007) Phaser crystallographic software. *J Appl Crystallogr* 40(Pt 4):658
18. Pathogenesis of Nasopharyngeal Carcinoma. *Cancer Res* 72(7): 1890-1900.
19. Kouvaraki M A, et al. (2006) Potential role of Jun activation domain-binding protein 1 as a negative regulator of p27kip1 in pancreatic adenocarcinoma. *Cancer Res* 66(17):8581-8589.
20. Krissinel E & Henrick K (2007) Inference of macromolecular assemblies from crystalline state. *J Mol Biol* 372(3):774-797.

21. Fang L, et al. (2008) Characterization of the human COP9 signalosome complex using affinity purification and mass spectrometry. *J Proteome Res* 7(11):4914-4925.
22. Tomoda K, Yoneda-Kato N, Fukumoto A, Yamanaka S, & Kato J Y (2004) Multiple functions of Jab1 are required for early embryonic development and growth potential in mice. *J Biol Chem* 279(41):43013-43018.
23. Sanches M, Alves B S, Zanchin N I, & Guimaraes B G (2007) The crystal structure of the human Mov34 MPN domain reveals a metal-free dimer. *J Mol Biol* 370(5): 846-855.
24. Zhang H, Gao, Z.-Q., Wang, W.-J., Liu, G. F., Shtykova, E. V., Xu, J.-H., Li, L.-F., Su, X.-D., Dong, Y.-H. (2012) The crystal structure of the MPN domain from the COPS signalosome subunit CSN6. *FEBS Letters* 586(8):1147-1153.
25. Ambroggio X I, Rees D C, & Deshaies R J (2004) JAMM: a metalloprotease-like zinc site in the proteasome and signalosome. *PLoS Biol* 2(1):E2.
26. Pena V, Liu S, Bujnicki J M, Luhrmann R, & Wahl M C (2007) Structure of a multipartite protein-protein interaction domain in splicing factor prp8 and its link to retinitis pigmentosa. *Mol Cell* 25(4):615-624.
27. Sato Y, et al. (2008) Structural basis for specific cleavage of Lys 63-linked polyubiquitin chains. *Nature* 455(7211): 358-362.
28. Tran H J, Allen M D, Lowe J, & Bycroft M (2003) Structure of the Jab1/MPN domain and its implications for proteasome function. *Biochemistry* 42(39):11460-11465.
29. Holm L & Rosenstrom P (2010) Dali server: conservation mapping in 3D. *Nucleic Acids Res* 38(Web Server issue):W545-549.
30. Pettersen E F, et al. (2004) UCSF Chimera—a visualization system for exploratory research and analysis. *J Comput Chem* 25(13):1605-1612.
31. Whitby F G, Xia G, Pickart C M, & Hill C P (1998) Crystal structure of the human ubiquitin-like protein NEDD8 and interactions with ubiquitin pathway enzymes. *J Biol Chem* 273(52):34983-34991.
32. Ramage R, et al. (1994) Synthetic, structural and biological studies of the ubiquitin system: the total chemical synthesis of ubiquitin. *Biochem J* 299 (Pt 1):151-158.
33. Ho B K & Agard D A (2009) Probing the flexibility of large conformational changes in protein structures through local perturbations. *PLoS Comput Biol* 5(4): e1000343.

Throughout this application, various references describe the state of the art to which this invention pertains. The disclosures of these references are hereby incorporated by reference into the present disclosure.

The invention claimed is:

1. A polypeptide comprising:
an amino acid sequence that has at least 85% sequence identity to amino acid residues 53-252 of SEQ ID NO: 1 wherein the amino acid residue of the polypeptide at the position corresponding to position 106 in SEQ ID NO: 1 is substituted by any amino acid except proline.

2. The polypeptide according to claim 1 comprising:
an amino acid sequence that has at least 85% sequence identity to SEQ ID NO: 1 wherein the amino acid residue of the polypeptide at the position corresponding to position 106 in SEQ ID NO: 1 is substituted by any amino acid except proline.

3. A kit of parts comprising:
a polypeptide according to claim 1, and
at least one CSN6 polypeptide, wherein said CSN6 polypeptide comprises an amino acid sequence that has at least 85% sequence identity to any one of SEQ ID NOs: 17-25.

* * * * *

SEQUENCE LISTING

```
<160> NUMBER OF SEQ ID NOS: 25

<210> SEQ ID NO 1
<211> LENGTH: 379
<212> TYPE: PRT
<213> ORGANISM: Homo sapiens

<400> SEQUENCE: 1

Met Val Ser Thr Asn Phe Thr Ser Gly Ser Arg Cys His Gly Cys Pro
1               5                   10                  15

Lys Ser Leu Glu Thr Thr Thr Ser Pro Leu Pro Arg Arg Trp Arg Arg
            20                  25                  30

Pro Gly Ala Val Trp Pro Arg Lys Pro Gly Asn Trp Pro Thr Thr Cys
        35                  40                  45

Arg Lys Leu Arg Val Ser Met Lys Ser Thr Asn Thr Thr Arg Asn Ser
    50                  55                  60

Ser Lys Lys Ser Trp Arg Arg Ser Pro Gly Leu Arg Ile Lys Gly Glu
65                  70                  75                  80

Ala Lys Ile Ser Ile His Val Leu Thr Ser Asn Met Ser His His Tyr
                85                  90                  95

Phe Lys Tyr Cys Lys Ile Ser Ala Leu Ala Leu Leu Lys Met Val Met
            100                 105                 110

His Ala Arg Ser Gly Gly Asn Leu Glu Val Met Gly Leu Met Leu Gly
        115                 120                 125

Lys Val Asp Gly Glu Thr Met Ile Ile Met Asp Ser Phe Ala Leu Pro
    130                 135                 140

Val Glu Gly Thr Glu Thr Arg Val Asn Ala Gln Ala Ala Tyr Glu
145                 150                 155                 160

Tyr Met Ala Ala Tyr Ile Glu Asn Ala Lys Gln Val Gly Arg Leu Glu
                165                 170                 175

Asn Ala Ile Gly Trp Tyr His Ser His Pro Gly Tyr Gly Cys Trp Leu
            180                 185                 190
```

```
Ser Gly Ile Asp Val Ser Thr Gln Met Leu Asn Gln Gln Phe Gln Glu
            195                 200                 205

Pro Phe Val Ala Val Val Ile Asp Pro Thr Arg Thr Ile Ser Ala Gly
    210                 215                 220

Lys Val Asn Leu Gly Ala Phe Arg Thr Tyr Pro Lys Gly Tyr Lys Pro
225                 230                 235                 240

Pro Asp Glu Gly Pro Ser Glu Tyr Gln Thr Ile Pro Leu Asn Lys Ile
                245                 250                 255

Glu Asp Phe Gly Val His Cys Lys Gln Tyr Tyr Ala Leu Glu Val Ser
                260                 265                 270

Tyr Phe Lys Ser Ser Leu Asp Arg Lys Leu Leu Glu Leu Leu Trp Asn
    275                 280                 285

Lys Tyr Trp Val Asn Thr Leu Ser Ser Ser Leu Leu Thr Asn Ala
290                 295                 300

Asp Tyr Thr Thr Gly Gln Val Phe Asp Leu Ser Glu Lys Leu Glu Gln
305                 310                 315                 320

Ser Glu Ala Gln Leu Gly Arg Gly Ser Phe Met Leu Gly Leu Glu Thr
                325                 330                 335

His Asp Arg Lys Ser Glu Asp Lys Leu Ala Lys Ala Thr Arg Asp Ser
                340                 345                 350

Cys Lys Thr Thr Ile Glu Ala Ile His Gly Leu Met Ser Gln Val Ile
            355                 360                 365

Lys Asp Lys Leu Phe Asn Gln Ile Asn Ile Ser
            370                 375

<210> SEQ ID NO 2
<211> LENGTH: 379
<212> TYPE: PRT
<213> ORGANISM: Homo sapiens

<400> SEQUENCE: 2

Met Val Ser Thr Asn Phe Thr Ser Gly Ser Arg Cys His Gly Cys Pro
1               5                   10                  15

Lys Ser Leu Glu Thr Thr Thr Ser Pro Leu Pro Arg Arg Trp Arg Arg
            20                  25                  30

Pro Gly Ala Val Trp Pro Arg Lys Pro Gly Asn Trp Pro Thr Thr Cys
        35                  40                  45

Arg Lys Leu Arg Val Ser Met Lys Ser Thr Asn Thr Thr Arg Asn Ser
50                  55                  60

Ser Lys Lys Ser Trp Arg Arg Ser Pro Gly Leu Arg Ile Lys Gly Glu
65                  70                  75                  80

Ala Lys Ile Ser Ile His Val Leu Thr Ser Asn Met Ser His Tyr
                85                  90                  95

Phe Lys Tyr Cys Lys Ile Ser Ala Leu Ala Leu Leu Lys Met Val Met
                100                 105                 110

His Ala Arg Ser Gly Gly Asn Leu Glu Val Met Gly Leu Met Leu Gly
            115                 120                 125

Lys Val Asp Gly Glu Thr Met Ile Ile Met Asp Ser Phe Ala Leu Pro
130                 135                 140

Val Glu Gly Thr Glu Thr Arg Val Asn Ala Gln Ala Ala Ala Tyr Glu
145                 150                 155                 160

Tyr Met Ala Ala Tyr Ile Glu Asn Ala Lys Gln Val Gly Arg Leu Glu
                165                 170                 175

Asn Ala Ile Gly Trp Tyr His Ser His Pro Gly Tyr Gly Cys Trp Leu
            180                 185                 190
```

```
Ser Gly Ile Asp Val Ser Thr Gln Met Leu Asn Gln Gln Phe Gln Glu
        195                 200                 205

Pro Phe Val Ala Val Val Ile Asp Pro Thr Arg Thr Ile Ser Ala Gly
210                 215                 220

Lys Val Asn Leu Gly Ala Phe Arg Thr Tyr Pro Lys Gly Tyr Lys Pro
225                 230                 235                 240

Pro Asp Glu Gly Pro Ser Glu Tyr Gln Thr Ile Pro Leu Asn Lys Ile
                245                 250                 255

Glu Asp Phe Gly Val His Cys Lys Gln Tyr Tyr Ala Leu Glu Val Ser
                260                 265                 270

Tyr Phe Lys Ser Ser Leu Asp Arg Lys Leu Leu Glu Leu Leu Trp Asn
            275                 280                 285

Lys Tyr Trp Val Asn Thr Leu Ser Ser Ser Leu Leu Thr Asn Ala
            290                 295                 300

Asp Tyr Thr Thr Gly Gln Val Phe Asp Leu Ser Glu Lys Leu Glu Gln
305                 310                 315                 320

Ser Glu Ala Gln Leu Gly Arg Gly Ser Phe Met Leu Gly Leu Glu Thr
                325                 330                 335

His Asp Arg Lys Ser Glu Asp Lys Leu Ala Lys Ala Thr Arg Asp Ser
                340                 345                 350

Cys Lys Thr Thr Ile Glu Ala Ile His Gly Leu Met Ser Gln Val Ile
            355                 360                 365

Lys Asp Lys Leu Phe Asn Gln Ile Asn Ile Ser
370                 375

<210> SEQ ID NO 3
<211> LENGTH: 339
<212> TYPE: PRT
<213> ORGANISM: Taeniopygia guttata

<400> SEQUENCE: 3

Met Ala Ala Ala Gly Ser Gly Ala Ser Gly Ser Gly Met Ala Gln Lys
1               5                   10                  15

Thr Trp Glu Leu Ala Asn Asn Met Gln Glu Ala Gln Ser Ile Asp Glu
            20                  25                  30

Ile Tyr Lys Tyr Asp Arg Lys Gln Gln Gln Glu Ile Leu Ala Ala Lys
        35                  40                  45

Pro Trp Thr Lys Asp His His Tyr Phe Lys Tyr Cys Lys Ile Ser Ala
50                  55                  60

Leu Ala Leu Leu Lys Met Val Met His Ala Arg Ser Gly Gly Asn Leu
65                  70                  75                  80

Glu Val Met Gly Leu Met Leu Gly Lys Val Asp Gly Glu Thr Met Ile
                85                  90                  95

Ile Met Asp Ser Phe Ala Leu Pro Val Glu Gly Thr Glu Thr Arg Val
            100                 105                 110

Asn Ala Gln Ala Ala Ala Tyr Glu Tyr Met Ala Ala Tyr Ile Glu Asn
        115                 120                 125

Ala Lys Gln Val Gly Arg Leu Glu Asn Ala Ile Gly Trp Tyr His Ser
130                 135                 140

His Pro Gly Tyr Gly Cys Trp Leu Ser Gly Ile Asp Val Ser Thr Gln
145                 150                 155                 160

Met Leu Asn Gln Gln Phe Gln Glu Pro Phe Val Ala Val Val Ile Asp
                165                 170                 175

Pro Thr Arg Thr Ile Ser Ala Gly Lys Val Asn Leu Gly Ala Phe Arg
```

```
                   180                 185                 190
Thr Tyr Pro Lys Gly Tyr Lys Pro Pro Asp Glu Gly Pro Ser Glu Tyr
            195                 200                 205
Gln Thr Ile Pro Leu Asn Lys Ile Glu Asp Phe Gly Val His Cys Lys
            210                 215                 220
Gln Tyr Tyr Ala Leu Glu Val Ser Tyr Phe Lys Ser Ser Leu Asp Arg
225                 230                 235                 240
Lys Leu Leu Glu Leu Leu Trp Asn Lys Tyr Trp Val Asn Thr Leu Ser
                245                 250                 255
Ser Ser Ser Leu Leu Thr Asn Ala Asp Tyr Thr Thr Gly Gln Val Phe
                260                 265                 270
Asp Leu Ser Glu Lys Leu Glu Gln Ser Glu Ala Gln Leu Gly Arg Gly
            275                 280                 285
Ser Phe Met Leu Gly Leu Glu Thr His Asp Lys Lys Ser Glu Asp Lys
            290                 295                 300
Leu Ala Lys Ala Thr Arg Asp Ser Cys Lys Thr Thr Ile Glu Ala Ile
305                 310                 315                 320
His Gly Leu Met Ser Gln Val Ile Lys Asp Lys Leu Phe Asn Gln Ile
                325                 330                 335
Asn Ile Ala

<210> SEQ ID NO 4
<211> LENGTH: 338
<212> TYPE: PRT
<213> ORGANISM: Gallus gallus

<400> SEQUENCE: 4

Met Ala Ala Ala Ser Gly Ser Ser Gly Ser Gly Met Ala Gln Lys Thr
1               5                   10                  15
Trp Glu Leu Ala Asn Asn Met Gln Glu Ala Gln Ser Ile Asp Glu Ile
                20                  25                  30
Tyr Lys Tyr Asp Arg Lys Gln Gln Gln Glu Ile Leu Ala Ala Lys Pro
            35                  40                  45
Trp Thr Lys Asp His His Tyr Phe Lys Tyr Cys Lys Ile Ser Ala Leu
        50                  55                  60
Ala Leu Leu Lys Met Val Met His Ala Arg Ser Gly Gly Asn Leu Glu
65              70                  75                  80
Val Met Gly Leu Met Leu Gly Lys Val Asp Gly Glu Thr Met Ile Ile
                85                  90                  95
Met Asp Ser Phe Ala Leu Pro Val Glu Gly Thr Glu Thr Arg Val Asn
            100                 105                 110
Ala Gln Ala Ala Tyr Glu Tyr Met Ala Ala Tyr Ile Glu Asn Ala
            115                 120                 125
Lys Gln Val Gly Arg Leu Glu Asn Ala Ile Gly Trp Tyr His Ser His
            130                 135                 140
Pro Gly Tyr Gly Cys Trp Leu Ser Gly Ile Asp Val Ser Thr Gln Met
145                 150                 155                 160
Leu Asn Gln Gln Phe Gln Glu Pro Phe Val Ala Val Ile Asp Pro
                165                 170                 175
Thr Arg Thr Ile Ser Ala Gly Lys Val Asn Leu Gly Ala Phe Arg Thr
            180                 185                 190
Tyr Pro Lys Gly Tyr Lys Pro Pro Asp Glu Gly Pro Ser Glu Tyr Gln
            195                 200                 205
Thr Ile Pro Leu Asn Lys Ile Glu Asp Phe Gly Val His Cys Lys Gln
```

```
            210                 215                 220
Tyr Tyr Ala Leu Glu Val Ser Tyr Phe Lys Ser Ser Leu Asp Arg Lys
225                 230                 235                 240

Leu Leu Glu Leu Leu Trp Asn Lys Tyr Trp Val Asn Thr Leu Ser Ser
                245                 250                 255

Ser Ser Leu Leu Thr Asn Ala Asp Tyr Thr Thr Gly Gln Val Phe Asp
                260                 265                 270

Leu Ser Glu Lys Leu Glu Gln Ser Glu Ala Gln Leu Gly Arg Gly Ser
                275                 280                 285

Phe Met Leu Gly Leu Glu Thr His Asp Lys Lys Ser Glu Asp Lys Leu
            290                 295                 300

Ala Lys Ala Thr Arg Asp Ser Cys Lys Thr Thr Ile Glu Ala Ile His
305                 310                 315                 320

Gly Leu Met Ser Gln Val Ile Lys Asp Lys Leu Phe Asn Gln Ile Asn
                325                 330                 335

Ile Ala

<210> SEQ ID NO 5
<211> LENGTH: 336
<212> TYPE: PRT
<213> ORGANISM: Cricetulus griseus

<400> SEQUENCE: 5

Met Pro Asp Asp Gly Ala Gly Ser Gly Met Ala Gln Lys Thr Trp Glu
1               5                   10                  15

Leu Ala Asn Asn Met Gln Glu Ala Gln Ser Ile Asp Glu Ile Tyr Lys
                20                  25                  30

Tyr Asp Lys Lys Gln Gln Gln Glu Ile Leu Ala Ala Lys Pro Trp Thr
            35                  40                  45

Lys Asp His His Tyr Phe Lys Tyr Cys Lys Ile Ser Ala Leu Ala Leu
        50                  55                  60

Leu Lys Met Val Met His Ala Arg Ser Gly Asn Leu Glu Val Met
65                  70                  75                  80

Gly Leu Met Leu Gly Lys Val Asp Gly Glu Thr Met Ile Ile Met Asp
                85                  90                  95

Ser Phe Ala Leu Pro Val Glu Gly Thr Glu Thr Arg Val Asn Ala Gln
                100                 105                 110

Ala Ala Ala Tyr Glu Tyr Met Ala Ala Tyr Ile Glu Asn Ala Lys Gln
            115                 120                 125

Val Gly Arg Leu Glu Asn Ala Ile Gly Trp Tyr His Ser His Pro Gly
        130                 135                 140

Tyr Gly Cys Trp Leu Ser Gly Ile Asp Val Ser Thr Gln Met Leu Asn
145                 150                 155                 160

Gln Gln Phe Gln Glu Pro Phe Val Ala Val Ile Asp Pro Thr Arg
                165                 170                 175

Thr Ile Ser Ala Gly Lys Val Asn Leu Gly Ala Phe Arg Thr Tyr Pro
            180                 185                 190

Lys Gly Tyr Lys Pro Pro Asp Glu Gly Pro Ser Glu Tyr Gln Thr Ile
        195                 200                 205

Pro Leu Asn Lys Ile Glu Asp Phe Gly Val His Cys Lys Gln Tyr Tyr
    210                 215                 220

Ala Leu Glu Val Ser Tyr Phe Lys Ser Ser Leu Asp Arg Lys Leu Leu
225                 230                 235                 240

Glu Leu Leu Trp Asn Lys Tyr Trp Val Asn Thr Leu Ser Ser Ser Ser
```

```
                    245                 250                 255
Leu Leu Thr Asn Ala Asp Tyr Thr Thr Gly Gln Val Phe Asp Leu Ser
            260                 265                 270

Glu Lys Leu Glu Gln Ser Glu Ala Gln Leu Gly Arg Gly Ser Phe Met
        275                 280                 285

Leu Gly Leu Glu Thr His Asp Arg Lys Ser Glu Asp Lys Leu Ala Lys
        290                 295                 300

Ala Thr Arg Asp Ser Cys Lys Thr Thr Ile Glu Ala Ile His Gly Leu
305                 310                 315                 320

Met Ser Gln Val Ile Lys Asp Lys Leu Phe Asn Gln Ile Asn Val Ala
                325                 330                 335

<210> SEQ ID NO 6
<211> LENGTH: 337
<212> TYPE: PRT
<213> ORGANISM: Crotalus adamanteus

<400> SEQUENCE: 6

Met Ala Thr Ala Gly Pro Ser Gly Ser Gly Met Ala Gln Lys Thr Trp
1               5                   10                  15

Glu Leu Thr Asn Asn Met Gln Glu Ala Gln Ser Ile Asp Glu Ile Tyr
            20                  25                  30

Lys Tyr Asp Arg Lys Gln Gln Gln Glu Ile Leu Ala Ala Lys Pro Trp
        35                  40                  45

Thr Lys Asp His His Tyr Phe Lys Tyr Cys Lys Ile Ser Ala Leu Ala
    50                  55                  60

Leu Leu Lys Met Val Met His Ala Arg Ser Gly Asn Leu Glu Val
65                  70                  75                  80

Met Gly Leu Met Leu Gly Lys Val Asp Gly Glu Thr Met Ile Ile Met
                85                  90                  95

Asp Ser Phe Ala Leu Pro Val Glu Gly Thr Glu Thr Arg Val Asn Ala
            100                 105                 110

Gln Ala Ala Ala Tyr Glu Tyr Met Ala Ala Tyr Ile Glu Asn Ala Lys
        115                 120                 125

Gln Val Gly Arg Leu Glu Asn Ala Ile Gly Trp Tyr His Ser His Pro
    130                 135                 140

Gly Tyr Gly Cys Trp Leu Ser Gly Ile Asp Val Ser Thr Gln Met Leu
145                 150                 155                 160

Asn Gln Gln Phe Gln Glu Pro Phe Val Ala Val Ile Asp Pro Thr
                165                 170                 175

Arg Thr Ile Ser Ala Gly Lys Val Asn Leu Gly Ala Phe Arg Thr Tyr
            180                 185                 190

Pro Lys Gly Tyr Lys Pro Pro Asp Glu Gly Pro Ser Glu Tyr Gln Thr
        195                 200                 205

Ile Pro Leu Asn Lys Ile Glu Asp Phe Gly Val His Cys Lys Gln Tyr
    210                 215                 220

Tyr Ala Leu Glu Val Ser Tyr Phe Lys Ser Ser Leu Asp Arg Lys Leu
225                 230                 235                 240

Leu Glu Leu Leu Trp Asn Lys Tyr Trp Val Asn Thr Leu Ser Ser Ser
                245                 250                 255

Ser Leu Leu Thr Asn Ala Asp Tyr Thr Thr Gly Gln Val Phe Asp Leu
            260                 265                 270

Ser Glu Lys Leu Glu Gln Ser Glu Ala Gln Leu Gly Arg Gly Ser Phe
        275                 280                 285
```

```
Met Leu Gly Leu Glu Ser His Asp Arg Lys Ser Glu Asp Lys Leu Ala
    290                 295                 300
Lys Ala Thr Arg Asp Ser Cys Lys Thr Thr Ile Glu Ala Ile His Gly
305                 310                 315                 320
Leu Met Ser Gln Val Ile Lys Asp Lys Leu Phe Asn Gln Ile Asn Ile
                325                 330                 335
Ala
```

<210> SEQ ID NO 7
<211> LENGTH: 322
<212> TYPE: PRT
<213> ORGANISM: Mustela putorius

<400> SEQUENCE: 7

```
Asp Asn Phe Ser Asp Ser Ser Ala Met Ala Ser Gly Ser Gly Met
1               5                   10                  15
Ala Gln Lys Thr Trp Glu Leu Ala Asn Asn Met Gln Glu Ala Gln Ser
                20                  25                  30
Ile Asp Glu Ile Tyr Lys Tyr Asp Lys Lys Gln Gln Gln Glu Ile Leu
                35                  40                  45
Ala Ala Lys Pro Trp Thr Lys Asp His His Tyr Phe Lys Tyr Cys Lys
50                  55                  60
Ile Ser Ala Leu Ala Leu Leu Lys Met Val Met His Ala Arg Ser Gly
65                  70                  75                  80
Gly Asn Leu Glu Val Met Gly Leu Met Leu Gly Lys Val Asp Gly Glu
                85                  90                  95
Thr Met Ile Ile Met Asp Ser Phe Ala Leu Pro Val Glu Gly Thr Glu
                100                 105                 110
Thr Arg Val Asn Ala Gln Ala Ala Ala Tyr Glu Tyr Met Ala Ala Tyr
                115                 120                 125
Ile Glu Asn Ala Lys Gln Val Gly Arg Leu Glu Asn Ala Ile Gly Trp
                130                 135                 140
Tyr His Ser His Pro Gly Tyr Gly Cys Trp Leu Ser Gly Ile Asp Val
145                 150                 155                 160
Ser Thr Gln Met Leu Asn Gln Gln Phe Gln Glu Pro Phe Val Ala Val
                165                 170                 175
Val Ile Asp Pro Thr Arg Thr Ile Ser Ala Gly Lys Val Asn Leu Gly
                180                 185                 190
Ala Phe Arg Thr Tyr Pro Lys Gly Tyr Lys Pro Pro Asp Glu Gly Pro
                195                 200                 205
Ser Glu Tyr Gln Thr Ile Pro Leu Asn Lys Ile Glu Asp Phe Gly Val
                210                 215                 220
His Cys Lys Gln Tyr Tyr Ala Leu Glu Val Ser Tyr Phe Lys Ser Ser
225                 230                 235                 240
Leu Asp Arg Lys Leu Leu Glu Leu Leu Trp Asn Lys Tyr Trp Val Asn
                245                 250                 255
Thr Leu Ser Ser Ser Leu Leu Thr Asn Ala Asp Tyr Thr Thr Gly
                260                 265                 270
Gln Val Phe Asp Leu Ser Glu Lys Leu Glu Gln Ser Glu Ala Gln Leu
                275                 280                 285
Gly Arg Gly Ser Phe Met Leu Gly Leu Glu Thr His Asp Arg Lys Ser
                290                 295                 300
Glu Asp Lys Leu Ala Lys Ala Thr Arg Asp Ser Cys Lys Thr Thr Ile
305                 310                 315                 320
```

Glu Ala

<210> SEQ ID NO 8
<211> LENGTH: 332
<212> TYPE: PRT
<213> ORGANISM: Xenopus laevis

<400> SEQUENCE: 8

```
Met Ala Gly Ser Ser Val Ala Gln Lys Thr Trp Glu Leu Ser Asn Asn
1               5                   10                  15

Met Gln Glu Val Gln Ser Ile Asp Glu Ile Tyr Lys Tyr Asp Lys Lys
            20                  25                  30

Gln Gln Gln Glu Ile Leu Ala Ala Lys Pro Trp Thr Lys Asp His His
        35                  40                  45

Tyr Phe Lys Tyr Cys Lys Val Ser Ala Leu Ala Leu Leu Lys Met Val
    50                  55                  60

Met His Ala Arg Ser Gly Gly Asn Leu Glu Val Met Gly Leu Met Leu
65                  70                  75                  80

Gly Lys Val Asp Gly Glu Thr Met Ile Ile Met Asp Ser Phe Ala Leu
                85                  90                  95

Pro Val Glu Gly Thr Glu Thr Arg Val Asn Ala Gln Ala Ala Ala Tyr
            100                 105                 110

Glu Tyr Met Ala Ala Tyr Ile Glu Asn Ala Lys Gln Val Gly Arg Leu
        115                 120                 125

Glu Asn Ala Ile Gly Trp Tyr His Ser His Pro Gly Tyr Gly Cys Trp
130                 135                 140

Leu Ser Gly Ile Asp Val Ser Thr Gln Met Leu Asn Gln Gln Phe Gln
145                 150                 155                 160

Glu Pro Phe Val Ala Val Val Ile Asp Pro Thr Arg Thr Ile Ser Ala
                165                 170                 175

Gly Lys Val Asn Leu Gly Ala Phe Arg Thr Tyr Pro Lys Gly Tyr Lys
            180                 185                 190

Pro Pro Asp Glu Gly Pro Ser Glu Tyr Gln Thr Ile Pro Leu Asn Lys
        195                 200                 205

Ile Glu Asp Phe Gly Val His Cys Lys Gln Tyr Tyr Ala Leu Glu Val
210                 215                 220

Thr Tyr Phe Lys Ser Ser Leu Asp Arg Lys Leu Leu Glu Leu Leu Trp
225                 230                 235                 240

Asn Lys Tyr Trp Val Asn Thr Leu Ser Ser Ser Leu Leu Thr Asn
                245                 250                 255

Ala Glu Tyr Thr Thr Gly Gln Val Phe Asp Leu Ser Glu Lys Leu Glu
            260                 265                 270

Gln Ser Glu Ala Gln Leu Gly Arg Gly Ser Phe Met Leu Gly Leu Glu
        275                 280                 285

Ser His Asp Arg Lys Ser Glu Asp Lys Leu Ala Lys Ala Thr Arg Asp
290                 295                 300

Ser Cys Lys Thr Thr Ile Glu Ala Ile His Gly Leu Met Ser Gln Val
305                 310                 315                 320

Ile Lys Asp Lys Leu Phe Asn Gln Ile Asn Thr Phe
                325                 330
```

<210> SEQ ID NO 9
<211> LENGTH: 333
<212> TYPE: PRT
<213> ORGANISM: Tetraodon nigroviridis

<400> SEQUENCE: 9

Ala Met Ala Gly Ser Ser Thr Ala Gln Lys Thr Trp Glu Leu Thr Asn
1 5 10 15

Asn Met Gln Glu Val Gln Ser Ile Asp Glu Ile Tyr Lys Tyr Asp Lys
20 25 30

Lys Gln Gln Gln Glu Ile Leu Ala Ala Lys Pro Trp Thr Lys Asp His
35 40 45

His Tyr Phe Lys Tyr Cys Lys Ile Ser Ala Leu Ala Leu Leu Lys Met
50 55 60

Val Met His Ala Arg Ser Gly Gly Asn Leu Glu Val Met Gly Leu Met
65 70 75 80

Leu Gly Lys Val Asp Gly Glu Thr Met Ile Ile Met Asp Ser Phe Ala
85 90 95

Leu Pro Val Glu Gly Thr Glu Thr Arg Val Asn Ala Gln Ala Ala Ala
100 105 110

Tyr Glu Tyr Met Ala Ala Tyr Ile Glu Asn Ala Lys Gln Val Gly Arg
115 120 125

Leu Glu Asn Ala Ile Gly Trp Tyr His Ser His Pro Gly Tyr Gly Cys
130 135 140

Trp Leu Ser Gly Ile Asp Val Ser Thr Gln Met Leu Asn Gln Gln Phe
145 150 155 160

Gln Glu Pro Phe Val Ala Val Val Ile Asp Pro Thr Arg Thr Ile Ser
165 170 175

Ala Gly Lys Val Asn Leu Gly Ala Phe Arg Thr Tyr Pro Lys Gly Tyr
180 185 190

Lys Pro Pro Asp Glu Gly Pro Ser Glu Tyr Gln Thr Ile Pro Leu Asn
195 200 205

Lys Ile Glu Asp Phe Gly Val His Cys Lys Gln Tyr Tyr Ala Leu Glu
210 215 220

Val Thr Tyr Phe Lys Ser Ser Leu Asp Arg Lys Leu Leu Glu Leu Leu
225 230 235 240

Trp Asn Lys Tyr Trp Val Asn Thr Leu Ser Ser Ser Ser Leu Leu Thr
245 250 255

Asn Ser Asp Tyr Thr Thr Gly Gln Val Phe Asp Leu Ser Glu Lys Leu
260 265 270

Glu Gln Ser Glu Ala Gln Leu Gly Arg Gly Ser Phe Met Leu Gly Leu
275 280 285

Asp Thr His Asp Arg Lys Ser Glu Asp Lys Leu Ala Lys Ala Thr Arg
290 295 300

Asp Ser Cys Lys Thr Thr Ile Glu Ala Ile His Gly Leu Met Ser Gln
305 310 315 320

Val Ile Lys Asp Lys Leu Phe Asn Gln Ile Asn Thr Ser
325 330

<210> SEQ ID NO 10
<211> LENGTH: 337
<212> TYPE: PRT
<213> ORGANISM: Amblyomma maculatum

<400> SEQUENCE: 10

Met Asp Asn His Met Ala Gln Lys Thr Trp Glu Met Ser Asn Asn Val
1 5 10 15

Glu Thr Val Gln Ser Val Asp Asp Leu Tyr Lys Tyr Asn Lys Lys Gln
20 25 30

```
Gln Gln Asp Ile Leu Thr Ala Lys Pro Trp Asp Lys Asp Pro His Tyr
            35                  40                  45

Phe Lys Asp Met Lys Val Ser Ala Leu Ala Leu Leu Lys Met Val Met
 50                  55                  60

His Ala Arg Ser Gly Gly Thr Leu Glu Val Met Gly Leu Leu Leu Gly
 65                  70                  75                  80

Lys Val Asp Ala Asn Thr Met Ile Val Met Asp Ser Phe Ala Leu Pro
                 85                  90                  95

Val Glu Gly Thr Glu Thr Arg Val Asn Ala Gln Ala Gln Ala Tyr Glu
            100                 105                 110

Tyr Met Ala Asp Tyr Thr Glu Asn Ala Lys Thr Val Gly Arg Leu Glu
            115                 120                 125

Asn Val Val Gly Trp Tyr His Ser His Pro Gly Tyr Gly Cys Trp Leu
130                 135                 140

Ser Gly Ile Asp Val Ser Thr Gln Met Leu Asn Gln Gln Phe Gln Glu
145                 150                 155                 160

Pro Phe Val Ala Ile Val Ile Asp Pro Val Arg Thr Ile Ser Ala Gly
                165                 170                 175

Lys Val Asn Leu Gly Ala Phe Arg Thr Tyr Pro Lys Gly Tyr Lys Pro
            180                 185                 190

Pro Asp Glu Gly Pro Ala Glu Tyr Gln Thr Ile Pro Leu Asn Lys Ile
            195                 200                 205

Glu Asp Phe Gly Val His Cys Lys Gln Tyr Tyr Ser Leu Glu Val Ser
            210                 215                 220

Tyr Phe Lys Ser Ser Leu Asp Arg Arg Leu Leu Asp Ser Leu Trp Asn
225                 230                 235                 240

Lys Tyr Trp Val Asn Thr Leu Ser Ser Ser Leu Leu Thr Asn Ala
                245                 250                 255

Asp Tyr Thr Thr Gly Gln Val Phe Asp Leu Ser Asp Lys Leu Glu Gln
                260                 265                 270

Ser Glu Ser Gln Leu Gly Arg Gly Gly Phe Val Leu Gly Leu Asp Pro
            275                 280                 285

His Glu Lys Arg Thr Glu Asp Lys Leu Ala Lys Ala Thr Arg Asp Ser
            290                 295                 300

Cys Lys Thr Thr Ile Glu Val Ile His Gly Leu Met Ser Gln Val Ile
305                 310                 315                 320

Lys Asp Arg Leu Phe Asn Gln Val Asn Val Ser Ser Thr Gln Asp Gln
                325                 330                 335

Leu

<210> SEQ ID NO 11
<211> LENGTH: 332
<212> TYPE: PRT
<213> ORGANISM: Crassostrea gigas

<400> SEQUENCE: 11

Met Asp Ser Lys Asn Ala Met Lys Thr Trp Glu Leu Ser Asn Asn Leu
  1               5                  10                  15

Glu Asn Val Ser Gly Val Asp Glu Ile Tyr Arg Tyr Asp Lys Lys Gln
             20                  25                  30

Gln Gln Asp Ile Leu Thr Ala Lys Pro Trp Glu Lys Asp Pro His Tyr
            35                  40                  45

Phe Lys His Ile Lys Val Ser Ala Leu Ala Leu Leu Lys Met Val Met
 50                  55                  60
```

His Ser Arg Ser Gly Gly Asn Leu Glu Val Met Gly Leu Leu Leu Gly
65                  70                  75                  80

Lys Val Asp Gly Asn Thr Met Ile Val Met Asp Ser Phe Ala Leu Pro
            85                  90                  95

Val Glu Gly Thr Glu Thr Arg Val Asn Ala Gln Ala Gln Ala Tyr Glu
        100                 105                 110

Tyr Met Ala Ala Tyr Thr Glu Ser Ala Lys Gln Val Gly Arg Leu Glu
        115                 120                 125

Asn Ala Ile Gly Trp Tyr His Ser His Pro Gly Tyr Gly Cys Trp Leu
130                 135                 140

Ser Gly Ile Asp Val Ser Thr Gln Met Leu Asn Gln Gln Phe Gln Glu
145                 150                 155                 160

Pro Phe Val Ala Ile Val Val Asp Pro Val Arg Thr Ile Ser Ala Gly
            165                 170                 175

Lys Val Asn Ile Gly Ala Phe Arg Thr Tyr Pro Lys Gly Phe Lys Pro
            180                 185                 190

Pro Asp Glu Gly Pro Ser Glu Tyr Gln Ser Ile Pro Leu Asn Lys Ile
        195                 200                 205

Glu Asp Phe Gly Val His Cys Lys His Tyr Tyr Ser Leu Asp Met Ser
210                 215                 220

Tyr Phe Lys Ser Val Ala Asp Arg Lys Leu Leu Glu Ser Leu Trp Asn
225                 230                 235                 240

Lys Tyr Trp Val Asn Thr Leu Ser Ser Ser Leu Leu Thr Asn Ala
            245                 250                 255

Asp Tyr Thr Thr Gly Gln Ile Phe Asp Leu Ala Asp Lys Leu Glu Gln
        260                 265                 270

Ser Glu Val Gln Leu Cys Arg Gly Gly Phe Met Leu Gly Met Asp Thr
        275                 280                 285

His Glu Lys Lys Ser Glu Asp Lys Leu Ala Lys Ala Thr Lys Asp Gly
        290                 295                 300

Cys Lys Thr Thr Met Glu Ala Ile His Gly Leu Met Ser Gln Val Ile
305                 310                 315                 320

Lys Asp Arg Leu Phe Asn Gln Val His Thr Thr Lys
            325                 330

<210> SEQ ID NO 12
<211> LENGTH: 348
<212> TYPE: PRT
<213> ORGANISM: Papilio xuthus

<400> SEQUENCE: 12

Met Ala Ser Thr Ser Ala Asp Ser Gln Ser Thr Thr Ala Gln Lys Thr
1               5                   10                  15

Trp Val Met Ala Asn Asn Ile Glu Thr Val Ser Ser Val Asp Glu Ile
            20                  25                  30

Tyr Arg Tyr Asp Lys Lys Gln Gln Gln Asp Ile Leu Ala Ala Lys Pro
        35                  40                  45

Trp Glu Lys Asp Pro His Phe Phe Lys Asp Ile Lys Ile Ser Ala Leu
    50                  55                  60

Ala Leu Leu Lys Met Val Met His Ala Arg Ser Gly Gly Thr Leu Glu
65                  70                  75                  80

Val Met Gly Leu Leu Leu Gly Lys Val Asp Ala Asn Thr Met Ile Val
            85                  90                  95

Met Asp Ser Phe Ala Leu Pro Val Glu Gly Thr Glu Thr Arg Val Asn
        100                 105                 110

Ala Gln Ala Gln Ala Tyr Glu Tyr Met Thr Ala Tyr Ile Glu Ala Ala
            115                 120                 125

Lys Gln Val Gly Arg His Glu Asn Ala Ile Gly Trp Tyr His Ser His
130                 135                 140

Pro Gly Tyr Gly Cys Trp Leu Ser Gly Ile Asp Val Ser Thr Gln Met
145                 150                 155                 160

Leu Asn Gln Asn Phe Gln Glu Pro Phe Val Ala Ile Val Ile Asp Pro
                165                 170                 175

Val Arg Thr Ile Ser Ala Gly Lys Val Cys Leu Gly Ala Phe Arg Thr
            180                 185                 190

Tyr Pro Lys Gly Tyr Lys Pro Ala Asn Glu Glu Pro Ser Glu Tyr Gln
        195                 200                 205

Thr Ile Pro Leu Asn Lys Ile Glu Asp Phe Gly Val His Cys Lys Gln
210                 215                 220

Tyr Tyr Ser Leu Glu Val Ser Tyr Phe Lys Ser Ser Leu Asp Arg Arg
225                 230                 235                 240

Leu Leu Asp Ser Leu Trp Asn Lys Tyr Trp Val Asn Thr Leu Ser Ser
                245                 250                 255

Ser Ser Leu Ile Thr Asn Ala Asp Tyr Thr Thr Gly Gln Ile Phe Asp
            260                 265                 270

Leu Ser Asp Lys Leu Glu Gln Ser Glu Val Cys Leu Ser Arg Gly Val
        275                 280                 285

Phe Leu Val Ala Gly Ala Asp Pro His Glu Lys Arg Ser Glu Asp Lys
290                 295                 300

Leu Ser Lys Ala Thr Lys Asp Ala Cys Lys Thr Thr Ile Glu Val Ile
305                 310                 315                 320

His Gly Leu Met Ala Gln Met Ile Lys Asp Arg Leu Phe Asn Gly Val
                325                 330                 335

Ser Gly Arg Pro Ala Pro Pro Thr Pro Met Ile Glu
            340                 345

<210> SEQ ID NO 13
<211> LENGTH: 348
<212> TYPE: PRT
<213> ORGANISM: Bombyx mori

<400> SEQUENCE: 13

Met Ala Ser Thr Ser Ala Asp Ser Gln Ala Ser Ile Ala Gln Lys Thr
1               5                   10                  15

Trp Val Met Ala Asn Asn Ile Glu Thr Val Ser Asn Val Asp Asp Ile
            20                  25                  30

Tyr Arg Tyr Asp Lys Lys Gln Gln Gln Asp Ile Leu Ala Ala Lys Pro
        35                  40                  45

Trp Glu Lys Asp Pro His Phe Phe Lys Asp Ile Lys Ile Ser Ala Leu
    50                  55                  60

Ala Leu Leu Lys Met Val Met His Ala Arg Ser Gly Gly Thr Leu Glu
65                  70                  75                  80

Val Met Gly Leu Leu Leu Gly Lys Val Asp Ala Asn Thr Met Ile Val
                85                  90                  95

Met Asp Ser Phe Ala Leu Pro Val Glu Gly Thr Glu Thr Arg Val Asn
            100                 105                 110

Ala Gln Ala Gln Ala Tyr Glu Tyr Met Thr Ala Tyr Ile Glu Ala Ala
        115                 120                 125

Lys Gln Val Gly Arg His Glu Asn Ala Ile Gly Trp Tyr His Ser His

```
            130                 135                 140
Pro Gly Tyr Gly Cys Trp Leu Ser Gly Ile Asp Val Ser Thr Gln Met
145                 150                 155                 160

Leu Asn Gln Asn Phe Gln Glu Pro Phe Val Ala Ile Val Ile Asp Pro
                165                 170                 175

Val Arg Thr Ile Ser Ala Gly Lys Val Cys Leu Gly Ala Phe Arg Thr
            180                 185                 190

Tyr Pro Lys Gly Tyr Lys Pro Ala Asn Glu Glu Pro Ser Glu Tyr Gln
        195                 200                 205

Thr Ile Pro Leu Asn Lys Ile Glu Asp Phe Gly Val His Cys Lys Gln
    210                 215                 220

Tyr Tyr Ser Met Glu Val Ser Tyr Phe Lys Ser Ser Leu Asp Arg Arg
225                 230                 235                 240

Leu Leu Asp Ser Leu Trp Asn Lys Tyr Trp Val Asn Thr Leu Ser Ser
                245                 250                 255

Ser Ser Leu Ile Thr Asn Ala Asp Tyr Thr Thr Gly Gln Ile Phe Asp
            260                 265                 270

Leu Ser Asp Lys Leu Glu Gln Ser Glu Val Cys Leu Gly Arg Gly Ala
        275                 280                 285

Phe Val Val Ala Gly Ala Asp Pro His Glu Lys Arg Thr Glu Asp Lys
    290                 295                 300

Leu Gly Lys Ala Thr Lys Asp Ala Cys Lys Thr Thr Ile Glu Val Ile
305                 310                 315                 320

His Gly Leu Met Ala Gln Met Ile Lys Asp Arg Leu Phe Asn Ser Val
                325                 330                 335

Cys Gly Arg Gln Ala Ala Pro Thr Pro Met Ile Glu
            340                 345

<210> SEQ ID NO 14
<211> LENGTH: 340
<212> TYPE: PRT
<213> ORGANISM: Anopheles gambiae

<400> SEQUENCE: 14

Met Glu Met Ala Arg Lys Thr Trp Glu Met Glu Asn Asn Ile Val Val
1               5                   10                  15

Leu Pro Pro Ser Asp Glu Ile Phe Arg Tyr Asp Ala Glu Gln Gln Gln
                20                  25                  30

Arg Ile Leu Thr Ala Arg Pro Trp Glu Lys Asp Pro Asn Phe Phe Lys
            35                  40                  45

Asp Ile Lys Ile Ser Ala Leu Ala Leu Ile Lys Met Val Thr His Ser
        50                  55                  60

Arg Ser Gly Gly Ala Leu Glu Val Met Gly Leu Leu Gly Lys Val
65                  70                  75                  80

Val Asp Asp Thr Met Val Met Asp Ala Phe Ala Leu Pro Val Glu
                85                  90                  95

Gly Thr Glu Thr Arg Val Asn Ala Gln Ser Gln Ala Tyr Glu Tyr Met
            100                 105                 110

Ala Ala Tyr Ile Glu Ser Ala Lys Glu Val Gly Arg Met Glu Asn Ala
        115                 120                 125

Ile Gly Trp Tyr His Ser His Pro Gly Tyr Gly Cys Trp Leu Ser Gly
    130                 135                 140

Ile Asp Val Asn Thr Gln Met Leu Asn Gln Asn Tyr Gln Glu Pro Phe
145                 150                 155                 160
```

```
Val Ala Ile Val Ile Asp Pro Val Arg Thr Val Ser Ala Gly Lys Val
                165                 170                 175
Cys Leu Gly Ala Phe Arg Thr Tyr Pro Lys Gly Tyr Lys Pro Pro Asn
            180                 185                 190
Glu Glu Pro Ser Glu Tyr Gln Thr Ile Pro Leu Ser Lys Ile Glu Asp
        195                 200                 205
Phe Gly Val His Cys Lys Gln Tyr Tyr Gln Leu Asp Val Thr Tyr Phe
    210                 215                 220
Lys Ser Ala Leu Asp Arg Lys Leu Leu Asp Ser Leu Trp Asn Lys Tyr
225                 230                 235                 240
Trp Met Asn Thr Leu Gly Ser Ser Gly Leu Leu Ser Asn Pro Asp Tyr
                245                 250                 255
Thr Thr Arg Gln Ile Leu Asp Leu Ser Glu Lys Leu Glu Leu Ser Glu
            260                 265                 270
Ala Ser Leu Gly Arg Gly Gln Phe Met Ala Ser Gly Ser Leu Asp Pro
        275                 280                 285
Asn Glu Lys Arg Thr Glu Asp Lys Leu Ser Lys Ala Ser Arg Asp Cys
    290                 295                 300
Ser Arg Ala Ser Ile Glu Leu Ile His Gly Leu Met Ala Gln Ile Ser
305                 310                 315                 320
Lys His Lys Leu Phe Asn Thr Ile Asn Thr Gly Glu Ala Lys Gly Ala
                325                 330                 335
Glu Asn Thr Ala
            340

<210> SEQ ID NO 15
<211> LENGTH: 344
<212> TYPE: PRT
<213> ORGANISM: Bombus impatiens

<400> SEQUENCE: 15

Met Ala Ser Thr Ser Ser Asp Gln Ser Thr Ile Ala Lys Lys Thr Trp
1               5                   10                  15
Glu Met Ser Asn Asn Ile Glu Thr Ile Ser Thr Val Asp Glu Ile Tyr
                20                  25                  30
Arg Tyr Asp Arg Lys Glu Gln Gln Asp Ile Leu Ala Ala Lys Pro Trp
            35                  40                  45
Glu Lys Asp Pro His Phe Phe Lys Asp Ile Lys Ile Ser Ala Leu Ala
        50                  55                  60
Leu Leu Lys Met Val Met His Ala Arg Ser Gly Gly Thr Leu Glu Val
65                  70                  75                  80
Met Gly Leu Leu Leu Gly Lys Val Ala Ala Asn Thr Met Ile Val Met
                85                  90                  95
Asp Ser Phe Ala Leu Pro Val Glu Gly Thr Glu Thr Arg Val Asn Ala
            100                 105                 110
Gln Ala Gln Ala Tyr Glu Tyr Met Thr Ala Tyr Ile Glu Ala Ala Lys
        115                 120                 125
Gln Val Gly Arg Gln Glu Asn Ala Ile Gly Trp Tyr His Ser His Pro
    130                 135                 140
Gly Tyr Gly Cys Trp Leu Ser Gly Ile Asp Val Ser Thr Gln Met Leu
145                 150                 155                 160
Asn Gln Asn Phe Gln Glu Pro Phe Val Ala Ile Val Ile Asp Pro Val
                165                 170                 175
Arg Thr Ile Ser Ala Gly Lys Val Cys Leu Gly Ala Phe Arg Thr Tyr
            180                 185                 190
```

```
Pro Lys Gly Tyr Lys Pro Ala Asn Glu Glu Pro Ser Glu Tyr Gln Thr
            195                 200                 205

Ile Pro Leu Asn Lys Ile Glu Asp Phe Gly Val His Cys Lys Gln Tyr
210                 215                 220

Tyr Ser Leu Glu Val Ser Tyr Phe Lys Ser Ser Leu Asp Arg Arg Leu
225                 230                 235                 240

Leu Asp Ser Leu Trp Asn Lys Tyr Trp Val Asn Thr Leu Ser Ser Ser
                245                 250                 255

Ser Leu Leu Thr Asn Ala Asp Tyr Thr Thr Gly Gln Ile Phe Asp Leu
            260                 265                 270

Ser Asp Lys Leu Glu Gln Ser Glu Val Ala Leu Gly Arg Gly Phe Ile
        275                 280                 285

Leu Gly Gly Thr Asp Pro His Asp Arg Ser Thr Val Glu Lys Leu Met
290                 295                 300

Lys Ala Thr Arg Asp Ser Cys Lys Thr Thr Ile Glu Ile Ile His Gly
305                 310                 315                 320

Leu Met Ala Gln Ile Ile Lys Asp Arg Leu Phe Asn Gln Val Gly Cys
                325                 330                 335

Asn Pro Ile Glu Thr Gln Gln Gln
            340

<210> SEQ ID NO 16
<211> LENGTH: 346
<212> TYPE: PRT
<213> ORGANISM: Schistosoma mansoni

<400> SEQUENCE: 16

Met Thr Thr Asn Lys Glu Val Val Pro Gln Gln Ser Ile Ser Gln Asn
1               5                   10                  15

Pro Val Leu Thr Asn Ser Pro Leu Asn Ala Ser Thr Ser Ala Arg Glu
            20                  25                  30

Gln Trp Glu Thr Glu Asn Asn Val Glu Ser Ile Leu Gly Pro Val Asp
        35                  40                  45

Glu Tyr Phe Lys Tyr Asp Val Lys Ile His Gln Ser Ile Val Asn Ala
50                  55                  60

Lys Pro Trp Glu Lys Asp Pro His Tyr Phe Lys Trp Ile Lys Ile Ser
65                  70                  75                  80

Ala Val Ala Leu Leu Lys Met Leu Ile His Ala Arg Ser Gly Gly Asn
                85                  90                  95

Leu Glu Met Gly Leu Leu Ile Gly Lys Val Ala His Gln Thr Met Ile
            100                 105                 110

Val Val Asp Ser Ser Pro Leu Pro Val Glu Gly Thr Glu Thr Arg Val
        115                 120                 125

Asn Ala Gln Ala Glu Ala Tyr Glu Tyr Met Thr Thr Tyr Lys Glu Val
130                 135                 140

Val Ala Arg Val Gly Arg Thr Glu Asn Val Leu Gly Trp Tyr His Ser
145                 150                 155                 160

His Pro Gly Tyr Gly Cys Trp Leu Ser Gly Ile Asp Val Ser Thr Gln
                165                 170                 175

Leu Thr Asn Gln Thr Tyr Gln Glu Pro Phe Val Ala Ile Val Ile Asp
            180                 185                 190

Pro Ile Arg Thr Ile Ser Ser Gly Lys Val Asn Leu Gly Ala Phe Arg
        195                 200                 205

Thr Tyr Pro Val Gly Tyr Arg Pro Pro Asp Asp Gly Pro Ser Glu Tyr
```

```
            210                 215                 220
Gln Ser Ile Pro Met Asp Lys Ile Glu Asp Phe Gly Val His Cys Lys
225                 230                 235                 240

His Tyr Tyr Ser Leu Glu Val Ser His Phe Lys Ser Val Leu Asp Lys
                245                 250                 255

Arg Leu Leu Asp Ser Leu Trp Asn Lys Tyr Trp Val Asn Thr Leu Ser
                260                 265                 270

Ser Val Ser Ile Leu Ala Gln Pro Asp Tyr Leu Ala Gly Leu Thr Lys
            275                 280                 285

Asp Leu Ala Glu Lys Val Glu His Ala Gly Ser Ser Met Ser Arg Met
290                 295                 300

Asn Trp Asp Asn Asp Arg Leu Glu Asp Arg Leu Ala Lys Cys Ser Lys
305                 310                 315                 320

Asp Ala Thr Lys Leu Ala Met Glu Gln Leu His Ala Leu Thr Gly Gln
                325                 330                 335

Leu Ile Lys Asp Ser Leu Phe Asn Lys Phe
                340                 345

<210> SEQ ID NO 17
<211> LENGTH: 327
<212> TYPE: PRT
<213> ORGANISM: Homo sapiens

<400> SEQUENCE: 17

Met Ala Ala Ala Ala Ala Ala Ala Thr Asn Gly Thr Gly Gly
1               5                   10                  15

Ser Ser Gly Met Glu Val Asp Ala Ala Val Val Pro Ser Val Met Ala
                20                  25                  30

Cys Gly Val Thr Gly Ser Val Ser Val Ala Leu His Pro Leu Val Ile
            35                  40                  45

Leu Asn Ile Ser Asp His Trp Ile Arg Met Arg Ser Gln Glu Gly Arg
        50                  55                  60

Pro Val Gln Val Ile Gly Ala Leu Ile Gly Lys Gln Glu Gly Arg Asn
65                  70                  75                  80

Ile Glu Val Met Asn Ser Phe Glu Leu Leu Ser His Thr Val Glu Glu
                85                  90                  95

Lys Ile Ile Ile Asp Lys Glu Tyr Tyr Tyr Thr Lys Glu Glu Gln Phe
            100                 105                 110

Lys Gln Val Phe Lys Glu Leu Glu Phe Leu Gly Trp Tyr Thr Thr Gly
        115                 120                 125

Gly Pro Pro Asp Pro Ser Asp Ile His Val His Lys Gln Val Cys Glu
130                 135                 140

Ile Ile Glu Ser Pro Leu Phe Leu Lys Leu Asn Pro Met Thr Lys His
145                 150                 155                 160

Thr Asp Leu Pro Val Ser Val Phe Glu Ser Val Ile Asp Ile Ile Asn
                165                 170                 175

Gly Glu Ala Thr Met Leu Phe Ala Glu Leu Thr Tyr Thr Leu Ala Thr
            180                 185                 190

Glu Glu Ala Glu Arg Ile Gly Val Asp His Val Ala Arg Met Thr Ala
        195                 200                 205

Thr Gly Ser Gly Glu Asn Ser Thr Val Ala Glu His Leu Ile Ala Gln
210                 215                 220

His Ser Ala Ile Lys Met Leu His Ser Arg Val Lys Leu Ile Leu Glu
225                 230                 235                 240
```

```
Tyr Val Lys Ala Ser Glu Ala Gly Glu Val Pro Phe Asn His Glu Ile
                245                 250                 255

Leu Arg Glu Ala Tyr Ala Leu Cys His Cys Leu Pro Val Leu Ser Thr
            260                 265                 270

Asp Lys Phe Lys Thr Asp Phe Tyr Asp Gln Cys Asn Asp Val Gly Leu
        275                 280                 285

Met Ala Tyr Leu Gly Thr Ile Thr Lys Thr Cys Asn Thr Met Asn Gln
    290                 295                 300

Phe Val Asn Lys Phe Asn Val Leu Tyr Asp Arg Gln Gly Ile Gly Arg
305                 310                 315                 320

Arg Met Arg Gly Leu Phe Phe
                325

<210> SEQ ID NO 18
<211> LENGTH: 324
<212> TYPE: PRT
<213> ORGANISM: Bos Taurus

<400> SEQUENCE: 18

Met Ala Thr Ala Ala Ala Asn Gly Thr Gly Gly Ser Ser Gly
1               5                   10                  15

Met Glu Val Asp Ala Val Val Pro Ser Val Met Ala Ser Gly Val
                20                  25                  30

Thr Gly Ser Val Ser Val Ala Leu His Pro Leu Val Ile Leu Asn Ile
            35                  40                  45

Ser Asp His Trp Ile Arg Met Arg Ser Gln Glu Gly Arg Pro Met Gln
    50                  55                  60

Val Ile Gly Ala Leu Ile Gly Lys Gln Glu Gly Arg Asn Ile Glu Val
65                  70                  75                  80

Met Asn Ser Phe Glu Leu Leu Ser His Thr Val Glu Glu Lys Ile Ile
                85                  90                  95

Ile Asp Lys Glu Tyr Tyr Tyr Thr Lys Glu Glu Gln Phe Lys Gln Val
            100                 105                 110

Phe Lys Glu Leu Asp Phe Leu Gly Trp Tyr Thr Thr Gly Gly Pro Pro
        115                 120                 125

Asp Pro Ser Asp Ile His Val His Lys Gln Val Cys Glu Ile Ile Glu
    130                 135                 140

Ser Pro Leu Phe Leu Lys Leu Asn Pro Met Thr Lys His Thr Asp Leu
145                 150                 155                 160

Pro Val Ser Val Phe Glu Ser Val Ile Asp Ile Ile Asn Gly Glu Ala
                165                 170                 175

Thr Met Leu Phe Ala Glu Leu Thr Tyr Thr Leu Ala Thr Glu Glu Ala
            180                 185                 190

Glu Arg Ile Gly Val Asp His Val Ala Arg Met Thr Ala Thr Gly Ser
        195                 200                 205

Gly Glu Asn Ser Thr Val Ala Glu His Leu Ile Ala Gln His Ser Ala
    210                 215                 220

Ile Lys Met Leu His Ser Arg Val Lys Leu Ile Leu Glu Tyr Val Lys
225                 230                 235                 240

Ala Ser Glu Ala Gly Glu Val Pro Phe Asn His Glu Ile Leu Arg Glu
                245                 250                 255

Ala Tyr Ala Leu Cys His Cys Leu Pro Val Leu Ser Thr Asp Lys Phe
            260                 265                 270

Lys Thr Asp Phe Tyr Asp Gln Cys Asn Asp Val Gly Leu Met Ala Tyr
        275                 280                 285
```

```
Leu Gly Thr Ile Thr Lys Thr Cys Asn Thr Met Asn Gln Phe Val Asn
        290                 295                 300

Lys Phe Asn Val Leu Tyr Asp Arg Gln Gly Ile Gly Arg Arg Met Arg
305                 310                 315                 320

Gly Leu Phe Phe

<210> SEQ ID NO 19
<211> LENGTH: 343
<212> TYPE: PRT
<213> ORGANISM: Cricetulus griseus

<400> SEQUENCE: 19

Met Arg Arg Ser Pro Thr Glu Ala Gly Lys Glu Gly Gly Pro Trp
1               5                   10                  15

Leu Ala Gly Ala Gly Lys Met Ala Ala Ala Ala Asn Gly Ser Gly
                20                  25                  30

Gly Ser Ser Gly Met Glu Val Asp Ala Ala Pro Ser Val Met Ala
                35                  40                  45

Ser Gly Val Thr Gly Ser Val Ser Val Ala Leu His Pro Leu Val Ile
50                  55                  60

Leu Asn Ile Ser Asp His Trp Ile Arg Met Arg Ser Gln Glu Gly Arg
65                  70                  75                  80

Pro Met Gln Val Ile Gly Ala Leu Ile Gly Lys Gln Glu Gly Arg Asn
                85                  90                  95

Ile Glu Val Met Asn Ser Phe Glu Leu Leu Ser His Thr Val Glu Glu
                100                 105                 110

Lys Ile Ile Ile Asp Lys Glu Tyr Tyr Tyr Thr Lys Glu Glu Gln Phe
                115                 120                 125

Lys Gln Val Phe Lys Glu Leu Glu Phe Leu Gly Trp Tyr Thr Thr Gly
                130                 135                 140

Gly Pro Pro Asp Pro Ser Asp Ile His Val His Lys Gln Val Cys Glu
145                 150                 155                 160

Ile Ile Glu Ser Pro Leu Phe Leu Lys Leu Asn Pro Met Thr Lys His
                165                 170                 175

Thr Asp Leu Pro Val Ser Val Phe Glu Ser Val Ile Asp Ile Ile Asn
                180                 185                 190

Gly Glu Ala Thr Met Leu Phe Ala Glu Leu Thr Tyr Thr Leu Ala Thr
                195                 200                 205

Glu Glu Ala Glu Arg Ile Gly Val Asp His Val Ala Arg Met Thr Ala
                210                 215                 220

Thr Gly Ser Gly Glu Asn Ser Thr Val Ala Glu His Leu Ile Ala Gln
225                 230                 235                 240

His Ser Ala Ile Lys Met Leu His Ser Arg Val Lys Leu Ile Leu Glu
                245                 250                 255

Tyr Val Lys Ala Ser Glu Ala Gly Glu Val Pro Phe Asn His Glu Ile
                260                 265                 270

Leu Arg Glu Ala Tyr Ala Leu Cys His Cys Leu Pro Val Leu Ser Thr
                275                 280                 285

Asp Lys Phe Lys Thr Asp Phe Tyr Asp Gln Cys Asn Asp Val Gly Leu
                290                 295                 300

Met Ala Tyr Leu Gly Thr Ile Thr Lys Thr Cys Asn Thr Met Asn Gln
305                 310                 315                 320

Phe Val Asn Lys Phe Asn Val Leu Tyr Asp Arg Gln Gly Ile Gly Arg
                325                 330                 335
```

```
Arg Met Arg Gly Leu Phe Phe
            340

<210> SEQ ID NO 20
<211> LENGTH: 316
<212> TYPE: PRT
<213> ORGANISM: Salmo salar

<400> SEQUENCE: 20

Met Ala Thr Ser Asn Gly Gly Met Glu Val Asp Gly Ala Ala Ser
1               5                   10                  15

Pro Ser Val Met Val Ser Gly Val Thr Gly Ser Val Ser Val Ala Leu
            20                  25                  30

His Pro Leu Val Ile Leu Asn Ile Ser Asp His Trp Ile Arg Ile Arg
        35                  40                  45

Ser Gln Glu Gly Arg Pro Met Gln Val Ile Gly Ala Leu Ile Gly Lys
    50                  55                  60

Gln Glu Gly Arg Asn Ile Glu Val Met Asn Ser Phe Glu Leu Leu His
65                  70                  75                  80

Gln Leu Val Asp Asp Arg Ala His Ile Asp Lys Glu Tyr Tyr Thr
                85                  90                  95

Lys Glu Glu Gln Phe Lys Gln Val Phe Lys Asp Met Glu Phe Leu Gly
            100                 105                 110

Trp Tyr Thr Thr Gly Gly Pro Cys Asp Gln Ser Asp Ile His Ile His
        115                 120                 125

Lys Gln Val Cys Glu Ile Ile Glu Ser Pro Leu Phe Leu Lys Leu Asn
    130                 135                 140

Pro Met Thr Lys His Thr Asp Leu Pro Val Ser Val Tyr Glu Ser Val
145                 150                 155                 160

Ile Asp Ile Ile Ser Gly Glu Ala Thr Met Leu Phe Ala Glu Leu Gly
                165                 170                 175

Tyr Thr Leu Ala Thr Glu Glu Ala Glu Arg Ile Gly Val Asp His Val
            180                 185                 190

Ala Arg Met Thr Ala Thr Gly Thr Gly Glu Asn Ser Thr Val Ala Glu
        195                 200                 205

His Leu Ile Ala Gln His Ser Ala Ile Lys Met Leu His Ser Arg Val
    210                 215                 220

Lys Val Ile Leu Glu Tyr Val Lys Ala Val Glu Ala Gly Glu Val Pro
225                 230                 235                 240

Phe Asn His Glu Ile Leu Arg Glu Ala Asn Ala Leu Cys His Arg Leu
                245                 250                 255

Pro Val Leu Ser Thr Ile Lys Phe Lys Thr Asp Phe Tyr Asp Gln Cys
            260                 265                 270

Asn Asp Val Gly Leu Met Ala Tyr Leu Gly Thr Ile Thr Lys Thr Cys
        275                 280                 285

Asn Ser Met Asn Gln Phe Ile Asn Lys Phe Asn Val Leu Tyr Asp Arg
    290                 295                 300

Gln Gly Ile Gly Arg Arg Met Arg Gly Leu Phe Phe
305                 310                 315

<210> SEQ ID NO 21
<211> LENGTH: 318
<212> TYPE: PRT
<213> ORGANISM: Xenopus laevis

<400> SEQUENCE: 21
```

Met Ala Ala Ala Ser Asn Gly Asn Gly Met Glu Val Asp Val Ala
1               5                   10                  15

Ala Leu Pro Ser Val Met Ala Gln Gly Val Thr Gly Ser Val Thr Val
                20                  25                  30

Ala Leu His Pro Leu Val Ile Leu Asn Ile Ser Asp His Trp Ile Arg
            35                  40                  45

Met Arg Ser Gln Glu Gly Arg Pro Met Gln Val Ile Gly Ala Leu Ile
        50                  55                  60

Gly Lys Gln Glu Gly Arg Asn Ile Glu Val Met Asn Ser Phe Glu Leu
65                  70                  75                  80

Leu Ser Gln Ile Asn Asp Glu Lys Ile Thr Ile Asn Lys Glu Tyr Tyr
                85                  90                  95

Tyr Thr Lys Glu Glu Gln Phe Lys Gln Val Phe Lys Asp Met Glu Phe
                100                 105                 110

Leu Gly Trp Tyr Thr Thr Gly Thr Pro Asp Pro Ser Asp Ile His
            115                 120                 125

Val His Lys Gln Val Cys Glu Ile Ile Glu Ser Pro Leu Phe Leu Lys
            130                 135                 140

Leu Asn Pro Met Thr Lys His Thr Asp Leu Pro Val Ser Val Tyr Glu
145                 150                 155                 160

Ser Val Ile Asp Ile Val Asn Gly Glu Ala Thr Met Leu Leu Ala Glu
                165                 170                 175

Leu Ser Tyr Thr Leu Ala Thr Glu Glu Ala Glu Arg Ile Gly Val Asp
            180                 185                 190

His Val Ala Arg Met Thr Ala Thr Gly Ser Gly Glu Asn Ser Thr Val
            195                 200                 205

Ala Glu His Leu Ile Ala Gln His Ser Ala Ile Lys Met Leu His Ser
210                 215                 220

Arg Val Arg Leu Ile Leu Glu Tyr Val Arg Ala Ala Glu Gly Gly Glu
225                 230                 235                 240

Val Pro Phe Asn His Glu Ile Leu Arg Glu Ala Ser Ala Leu Cys His
                245                 250                 255

Cys Leu Pro Val Leu Ser Thr Asp Lys Phe Lys Thr Asp Phe Tyr Asp
            260                 265                 270

Gln Cys Asn Asp Val Gly Leu Met Ser Tyr Leu Gly Thr Ile Thr Lys
            275                 280                 285

Thr Cys Asn Thr Met Asn Gln Phe Val Asn Lys Phe Asn Ile Leu Tyr
            290                 295                 300

Asp Arg Gln Gly Ile Gly Arg Arg Met Arg Gly Leu Phe Phe
305                 310                 315

<210> SEQ ID NO 22
<211> LENGTH: 323
<212> TYPE: PRT
<213> ORGANISM: Tetraodon nigroviridis

<400> SEQUENCE: 22

Leu Arg Ser Leu Pro Asp Lys Met Ala Thr Ser Asn Gly Gly Gly Met
1               5                   10                  15

Glu Val Asp Gly Ala Ala Ser Pro Ser Val Met Ala Ser Gly Val Thr
                20                  25                  30

Gly Ser Val Ser Val Ala Leu His Pro Leu Val Ile Leu Asn Ile Ser
            35                  40                  45

Asp His Trp Ile Arg Ile Arg Ser Gln Glu Gly Arg Pro Met Gln Val

```
            50                  55                  60
Ile Gly Ala Leu Ile Gly Lys Gln Glu Gly Arg Asn Ile Glu Val Met
 65                  70                  75                  80

Asn Ser Phe Glu Leu Leu Ser His Thr Ile Asp Asp Arg Val His Ile
                 85                  90                  95

Asp Lys Glu Tyr Tyr Tyr Thr Lys Glu Glu Gln Phe Lys Gln Val Phe
                100                 105                 110

Lys Asp Met Glu Phe Leu Gly Trp Tyr Thr Thr Gly Gly Pro Pro Asp
            115                 120                 125

Gln Ser Asp Ile His Ile His Lys Gln Val Cys Glu Ile Ile Glu Ser
            130                 135                 140

Pro Leu Phe Leu Lys Leu Asn Pro Met Thr Lys His Thr Asp Leu Pro
145                 150                 155                 160

Val Ser Val Tyr Glu Ser Val Ile Asp Ile Ile Ser Gly Glu Ala Thr
                165                 170                 175

Met Leu Phe Ala Glu Leu Thr Tyr Thr Leu Ala Thr Glu Glu Ala Glu
            180                 185                 190

Arg Ile Gly Val Asp His Val Ala Arg Met Thr Ala Thr Gly Thr Gly
            195                 200                 205

Glu Asn Ser Thr Val Ala Glu His Leu Ile Ala Gln His Ser Ala Ile
210                 215                 220

Lys Met Leu His Ser Arg Val Lys Ile Ile Leu Glu Tyr Val Lys Ala
225                 230                 235                 240

Val Glu Ala Gly Glu Val Pro Phe Asn His Glu Ile Leu Arg Glu Ala
                245                 250                 255

Asn Ala Leu Cys His Arg Leu Pro Val Leu Ser Thr Ser Lys Phe Lys
            260                 265                 270

Thr Asp Phe Tyr Asp Gln Cys Asn Asp Val Gly Leu Met Ala Tyr Leu
            275                 280                 285

Gly Thr Ile Thr Lys Thr Cys Asn Ser Met Asn Gln Phe Ile Asn Lys
            290                 295                 300

Phe Asn Ile Leu Tyr Asp Arg Gln Gly Ile Gly Arg Arg Met Arg Gly
305                 310                 315                 320

Leu Phe Phe

<210> SEQ ID NO 23
<211> LENGTH: 316
<212> TYPE: PRT
<213> ORGANISM: Anoplopoma fimbria

<400> SEQUENCE: 23

Met Ala Thr Ser Asn Gly Gly Met Glu Val Asp Gly Ala Ala Ser
 1               5                  10                  15

Pro Ser Val Met Ala Ala Gly Leu Thr Gly Ser Val Ser Val Ala Leu
                20                  25                  30

His Pro Leu Val Ile Leu Asn Ile Ser Asp His Trp Ile Arg Ile Arg
            35                  40                  45

Ser Gln Glu Gly Arg Pro Met Gln Val Ile Gly Ala Leu Ile Gly Lys
        50                  55                  60

Gln Glu Gly Arg Asn Ile Glu Val Met Asn Ser Phe Glu Leu Leu Ser
 65                  70                  75                  80

His Thr Ile Asp Glu Arg Val His Ile Asp Lys Glu Tyr Tyr Tyr Thr
                85                  90                  95

Lys Glu Glu Gln Phe Lys Gln Val Phe Lys Glu Met Glu Phe Leu Gly
```

```
            100                 105                 110
Trp Tyr Thr Thr Gly Gly Pro Pro Asp Ala Ser Asp Ile His Ile His
            115                 120                 125

Lys Gln Val Cys Glu Ile Ile Glu Ser Pro Leu Phe Leu Lys Leu Asn
            130                 135                 140

Pro Met Thr Lys His Thr Asp Leu Pro Val Ser Val Tyr Glu Ser Val
145                 150                 155                 160

Ile Asp Ile Ile Asn Gly Glu Ala Thr Met Leu Phe Ala Glu Leu Thr
            165                 170                 175

Tyr Thr Leu Ala Thr Glu Glu Ala Glu Arg Ile Gly Val Asp His Val
            180                 185                 190

Ala Arg Met Thr Ala Thr Gly Thr Gly Glu Asn Ser Thr Val Ala Glu
            195                 200                 205

His Leu Ile Ala Gln His Ser Ala Ile Lys Met Leu His Ser Arg Val
            210                 215                 220

Lys Ile Ile Leu Glu Tyr Val Lys Ala Val Glu Ser Gly Glu Val Pro
225                 230                 235                 240

Phe Asn His Glu Ile Leu Arg Glu Ala Asn Ala Leu Cys His Arg Leu
            245                 250                 255

Pro Val Leu Ser Thr Ile Lys Phe Lys Thr Asp Phe Tyr Asp Gln Cys
            260                 265                 270

Asn Asp Val Gly Leu Met Ala Tyr Leu Gly Thr Ile Thr Lys Thr Cys
            275                 280                 285

Asn Ser Met Asn Gln Phe Ile Asn Lys Phe Asn Val Leu Tyr Asp Arg
            290                 295                 300

Gln Gly Ile Gly Arg Arg Met Arg Gly Leu Phe Phe
305                 310                 315

<210> SEQ ID NO 24
<211> LENGTH: 312
<212> TYPE: PRT
<213> ORGANISM: Crassostrea gigas

<400> SEQUENCE: 24

Met Ala Gly Lys Met Glu Val Asp Gly Pro Gly Gly Gly Val Met Ala
1               5                   10                  15

Ser Thr Ser Cys Pro Gly Ser Val Ser Val Ser Leu His Pro Leu Val
            20                  25                  30

Ile Met Asn Ile Ser Glu His Trp Thr Arg Val Arg Ala Gln Glu Gly
            35                  40                  45

Lys Pro Thr Gln Val Leu Gly Ala Val Ile Gly Lys Gln Lys Gly Arg
            50                  55                  60

Lys Ile Glu Val Met Asn Ser Phe Glu Leu Leu Phe Asp Leu Ile Glu
65                  70                  75                  80

Gly Glu Ile Ile Val Asn Met Glu Tyr Tyr Asn Thr Lys Glu Glu Gln
            85                  90                  95

Phe Lys Gln Val Phe Ser Asp Leu Asp Phe Leu Gly Trp Tyr Ser Thr
            100                 105                 110

Gly Asp Thr Pro Thr Ser Ser Asp Ile Lys Ile His Lys Gln Ile Cys
            115                 120                 125

Gln Ile Asn Glu Ser Pro Ile Phe Val Arg Leu Asn Pro Leu Ala Arg
            130                 135                 140

Gln Ser Asp Leu Pro Val Thr Ile Phe Glu Ser Val Ile Asp Leu Val
145                 150                 155                 160
```

-continued

```
Asn Asn Glu Ala Thr Met Leu Phe Val Glu Leu Gln Tyr Thr Leu Ala
            165                 170                 175

Thr Glu Glu Ala Glu Arg Ile Gly Val Asp His Val Ala Arg Met Ser
        180                 185                 190

Thr Ser Asp Ala Gly Glu Gly Ser Ser Val Ala Glu His Leu Ile Ala
        195                 200                 205

Gln His Ser Ser Ile Lys Met Leu His Ser Arg Val Lys Leu Ile Leu
        210                 215                 220

Glu Tyr Ile Lys Ala Val Gln Ser Gly Glu Val Pro Lys Asn His Asp
225                 230                 235                 240

Ile Leu Arg Glu Ala Tyr Ser Leu Cys Tyr Arg Leu Pro Val Leu Asn
            245                 250                 255

Thr Pro Lys Phe Lys Glu Asp Phe Tyr Asn Gln Cys Asn Asp Val Cys
        260                 265                 270

Leu Met Ala Tyr Leu Gly Thr Ile Thr Lys Gly Cys Asn Thr Ile Asn
        275                 280                 285

Gln Phe Val Asn Lys Phe Asn Val Met Tyr Asp Arg Gln Gly Met Gly
        290                 295                 300

Arg Arg Met Arg Gly Leu Phe Phe
305                 310
```

<210> SEQ ID NO 25
<211> LENGTH: 341
<212> TYPE: PRT
<213> ORGANISM: Drosophila melanogaster

<400> SEQUENCE: 25

```
Met Glu Gln Met Glu Val Asp Val Asp Met Ser Ala Lys Pro Ser Thr
1               5                   10                  15

Ser Ser Ser Ala Ala Gly Ser Ser Met Ala Val Asp Lys Thr Ala
            20                  25                  30

Asp Gln Asn Pro Gln Pro Gln Gly Asn Ile Met Ala Ala Ala Gly Thr
        35                  40                  45

Ser Gly Ser Val Thr Ile Ser Leu His Pro Leu Val Ile Met Asn Ile
50                  55                  60

Ser Glu His Trp Thr Arg Phe Arg Ala Gln His Gly Glu Pro Arg Gln
65                  70                  75                  80

Val Tyr Gly Ala Leu Ile Gly Lys Gln Lys Gly Arg Asn Ile Glu Ile
            85                  90                  95

Met Asn Ser Phe Glu Leu Lys Thr Asp Val Ile Gly Asp Glu Thr Val
        100                 105                 110

Ile Asn Lys Asp Tyr Tyr Asn Lys Lys Glu Gln Gln Tyr Lys Gln Val
        115                 120                 125

Phe Ser Asp Leu Asp Phe Ile Gly Trp Tyr Thr Thr Gly Asp Asn Pro
        130                 135                 140

Thr Ala Asp Asp Ile Lys Ile Gln Arg Gln Ile Ala Ala Ile Asn Glu
145                 150                 155                 160

Cys Pro Ile Met Leu Gln Leu Asn Pro Leu Ser Arg Ser Val Asp His
            165                 170                 175

Leu Pro Leu Lys Leu Phe Glu Ser Leu Ile Asp Leu Val Asp Gly Glu
        180                 185                 190

Ala Thr Met Leu Phe Val Pro Leu Thr Tyr Thr Leu Ala Thr Glu Glu
        195                 200                 205

Ala Glu Arg Ile Gly Val Asp His Val Ala Arg Met Thr Ser Asn Glu
        210                 215                 220
```

-continued

```
Ser Gly Glu Lys Ser Val Val Ala Glu His Leu Val Ala Gln Asp Ser
225                 230                 235                 240

Ala Ile Lys Met Leu Asn Thr Arg Ile Lys Ile Val Leu Gln Tyr Ile
                245                 250                 255

Arg Asp Val Glu Ala Gly Lys Leu Arg Ala Asn Gln Glu Ile Leu Arg
            260                 265                 270

Glu Ala Tyr Ala Leu Cys His Arg Leu Pro Val Met Gln Val Pro Ala
            275                 280                 285

Phe Gln Glu Glu Phe Tyr Thr Gln Cys Asn Asp Val Gly Leu Ile Ser
        290                 295                 300

Tyr Leu Gly Thr Leu Thr Lys Gly Cys Asn Asp Met His His Phe Val
305                 310                 315                 320

Asn Lys Phe Asn Met Leu Tyr Asp Arg Gln Gly Ser Ala Arg Arg Met
                325                 330                 335

Arg Gly Leu Tyr Tyr
            340
```